(12) United States Patent
Cohen et al.

(10) Patent No.: US 11,723,728 B2
(45) Date of Patent: Aug. 15, 2023

(54) ACTUATION OF A DEVICE COMPRISING MECHANICAL ARMS

(71) Applicant: MEMIC INNOVATIVE SURGERY LTD, Or-Yehuda (IL)

(72) Inventors: Dvir Cohen, Ramot-Menashe (IL); Yaron Levinson, Tel-Aviv (IL)

(73) Assignee: Momentis Surgical Ltd., Or-Yehuda (IL)

( * ) Notice: Subject to any disclaimer, the term of this patent is extended or adjusted under 35 U.S.C. 154(b) by 277 days.

(21) Appl. No.: 15/930,914

(22) Filed: May 13, 2020

(65) Prior Publication Data

US 2020/0268458 A1 Aug. 27, 2020

Related U.S. Application Data

(63) Continuation of application No. 15/501,862, filed as application No. PCT/IL2016/050976 on Sep. 4, 2016,
(Continued)

(51) Int. Cl.
*A61B 34/30* (2016.01)
*B25J 9/10* (2006.01)
*B25J 18/02* (2006.01)
*A61B 34/00* (2016.01)
*A61B 17/29* (2006.01)

(52) U.S. Cl.
CPC .............. *A61B 34/30* (2016.02); *A61B 17/29* (2013.01); *A61B 34/70* (2016.02); *B25J 9/102* (2013.01); *B25J 18/025* (2013.01); *A61B 2034/301* (2016.02); *A61B 2034/306* (2016.02)

(58) Field of Classification Search
CPC combination set(s) only.
See application file for complete search history.

(56) References Cited

U.S. PATENT DOCUMENTS 2,165,478 A 7/1939 Gross
3,913,573 A 10/1975 Gutnick
(Continued)

FOREIGN PATENT DOCUMENTS

CN 101040773 9/2007
CN 102465957 5/2012
(Continued)

OTHER PUBLICATIONS

Office Action dated Apr. 28, 2020 From the Israel Patent Office Re. Application No. 250896 and its Translation Into English. (4 Pages).
(Continued)

*Primary Examiner* — Scott Luan
(74) *Attorney, Agent, or Firm* — Momentum IP; Marc Van Dyke

(57) ABSTRACT

Some embodiments of the invention relate to a mechanism for actuating a shaft having two degrees of freedom, comprising: a first actuator configured to rotate the shaft around the shaft axis, and a second actuator configured to bend the shaft using one or more elongated elements attached to the shaft, wherein actuation of the first actuator indirectly manipulates the elongated elements controlled by the second actuator, thereby affecting operation of the second actuator. Some embodiments relate to motorized actuation of a system comprising at least one surgical arm.

9 Claims, 21 Drawing Sheets

Related U.S. Application Data now abandoned, which is a continuation-in-part of application No. PCT/IL2015/050893, filed on Sep. 4, 2015, and a continuation-in-part of application No. PCT/IL2015/050892, filed on Sep. 4, 2015, and a continuation-in-part of application No. PCT/IL2016/050891, filed on Sep. 4, 2015.

(60) Provisional application No. 62/305,613, filed on Mar. 9, 2016.

(56) References Cited

U.S. PATENT DOCUMENTS

| | | |
|---|---|---|
| 4,054,131 A | 10/1977 | Kessel |
| 4,364,535 A | 12/1982 | Itoh et al. |
| 4,954,952 A | 9/1990 | Ubhayakar et al. |
| 5,597,146 A | 1/1997 | Putman |
| 5,624,398 A | 4/1997 | Smith et al. |
| 5,810,716 A | 9/1998 | Mukherjee et al. |
| 5,876,325 A | 3/1999 | Mizuno et al. |
| 6,168,611 B1 | 1/2001 | Rizvi |
| 6,231,565 B1 | 5/2001 | Tovey et al. |
| 6,331,181 B1 | 12/2001 | Tierney et al. |
| 6,425,865 B1 | 7/2002 | Salcudean et al. |
| 7,008,362 B2 | 3/2006 | Fitzgibbon |
| 7,371,210 B2 | 5/2008 | Brock et al. |
| 7,678,117 B2 | 3/2010 | Hinman et al. |
| 7,766,821 B2 | 8/2010 | Brunnen |
| 7,833,156 B2 | 11/2010 | Williams et al. |
| 7,918,845 B2 | 4/2011 | Saadat et al. |
| 8,224,485 B2 | 7/2012 | Unsworth |
| 8,347,754 B1 | 1/2013 | Veltri et al. |
| 8,518,024 B2 | 8/2013 | Williams et al. |
| 9,033,998 B1 | 5/2015 | Schaible et al. |
| 9,039,057 B2 | 5/2015 | Schvalb et al. |
| 9,357,984 B2 | 6/2016 | Malkowski |
| 9,662,176 B2 | 4/2017 | Cooper et al. |
| 9,788,911 B2 | 10/2017 | Cohen et al. |
| 9,820,822 B2 | 11/2017 | Cohen et al. |
| 10,022,197 B2 | 7/2018 | Cohen et al. |
| 10,052,165 B2 | 8/2018 | Cohen et al. |
| 10,070,930 B2 | 9/2018 | Cohen et al. |
| 10,278,683 B2 | 5/2019 | Robert et al. |
| 10,299,866 B2 | 5/2019 | Cohen et al. |
| 10,470,831 B2 | 11/2019 | Cohen et al. |
| 10,500,003 B2 | 12/2019 | Cohen et al. |
| 10,617,481 B2 | 4/2020 | Cohen et al. |
| 10,736,658 B2 | 8/2020 | Cohen et al. |
| 10,849,654 B2 | 12/2020 | Cohen et al. |
| 10,869,692 B2 | 12/2020 | Cohen et al. |
| 10,973,592 B2 | 4/2021 | Cohen et al. |
| 2001/0021854 A1 | 9/2001 | Donnez et al. |
| 2002/0087048 A1 | 7/2002 | Brock et al. |
| 2003/0004610 A1 | 1/2003 | Niemeyer et al. |
| 2003/0109780 A1 | 6/2003 | Coste-Maniere et al. |
| 2003/0109857 A1 | 6/2003 | Sanchez et al. |
| 2004/0044350 A1 | 3/2004 | Martin et al. |
| 2004/0128026 A1 | 7/2004 | Harris et al. |
| 2004/0138525 A1 | 7/2004 | Saadat et al. |
| 2004/0236316 A1 | 11/2004 | Danitz et al. |
| 2005/0059960 A1 | 3/2005 | Simaan et al. |
| 2005/0096694 A1 | 5/2005 | Lee |
| 2005/0272977 A1 | 12/2005 | Saadat et al. |
| 2006/0095022 A1 | 5/2006 | Moll et al. |
| 2006/0142657 A1 | 6/2006 | Quaid et al. |
| 2006/0206101 A1 | 9/2006 | Fee |
| 2006/0241414 A1 | 10/2006 | Nowlin et al. |
| 2007/0156019 A1 | 7/2007 | Larkin et al. |
| 2007/0221700 A1 | 9/2007 | Ortiz et al. |
| 2007/0287992 A1 | 12/2007 | Diolaiti et al. |
| 2008/0064921 A1 | 3/2008 | Larkin et al. |
| 2008/0065108 A1 | 3/2008 | Diolaiti |
| 2008/0119868 A1 | 5/2008 | Sharp et al. |
| 2008/0125869 A1 | 5/2008 | Paz et al. |
| 2009/0000626 A1 | 1/2009 | Quaid et al. |
| 2009/0012531 A1 | 1/2009 | Quaid et al. |
| 2009/0171373 A1 | 7/2009 | Fanitor et al. |
| 2010/0016659 A1 | 1/2010 | Weitzner |
| 2010/0170361 A1 | 7/2010 | Bennett et al. |
| 2010/0191278 A1 | 7/2010 | Fee et al. |
| 2010/0274087 A1 | 10/2010 | Diolaiti et al. |
| 2010/0292558 A1 | 11/2010 | Saadat et al. |
| 2010/0318100 A1 | 12/2010 | Okamoto et al. |
| 2011/0022052 A1 | 1/2011 | Jorgensen |
| 2011/0046441 A1 | 2/2011 | Wiltshire et al. |
| 2011/0082462 A1 | 4/2011 | Suarez et al. |
| 2011/0082468 A1 | 4/2011 | Hagag et al. |
| 2011/0105843 A1 | 5/2011 | Mueller |
| 2011/0118748 A1 | 5/2011 | Itkowitz |
| 2011/0264136 A1 | 10/2011 | Choi et al. |
| 2011/0276038 A1 | 11/2011 | Mcintyre et al. |
| 2011/0277775 A1 | 11/2011 | Holop et al. |
| 2012/0010629 A1 | 1/2012 | Mire et al. |
| 2012/0059392 A1 | 3/2012 | Diolaiti |
| 2012/0123207 A1 | 5/2012 | Vargas |
| 2012/0186383 A1 | 7/2012 | Schvalb et al. |
| 2012/0253131 A1 | 10/2012 | Malkowski et al. |
| 2013/0006267 A1 | 1/2013 | Odermatt et al. |
| 2013/0018303 A1 | 1/2013 | Webster et al. |
| 2013/0035697 A1 | 2/2013 | Ogawa et al. |
| 2013/0172904 A1 | 7/2013 | Ikits |
| 2013/0296882 A1 | 11/2013 | Kim et al. |
| 2014/0039517 A1 | 2/2014 | Bowling et al. |
| 2014/0046340 A1 | 2/2014 | Wilson et al. |
| 2014/0062113 A1 | 3/2014 | Kovarik et al. |
| 2014/0114293 A1 | 4/2014 | Jeong et al. |
| 2014/0222198 A1 | 8/2014 | Emami et al. |
| 2014/0276943 A1 | 9/2014 | Bowling et al. |
| 2014/0330432 A1 | 11/2014 | Simaan et al. |
| 2015/0038981 A1 | 2/2015 | Kilroy et al. |
| 2015/0230697 A1 | 8/2015 | Phee et al. |
| 2016/0081714 A1 | 3/2016 | Kobayashi et al. |
| 2016/0128790 A1 | 5/2016 | Ogawa et al. |
| 2016/0135909 A1 | 5/2016 | Ogawa et al. |
| 2016/0135911 A1 | 5/2016 | Yanagihara et al. |
| 2016/0144504 A1 | 5/2016 | Kuth et al. |
| 2016/0166343 A1 | 6/2016 | Poon et al. |
| 2017/0071587 A1 | 3/2017 | Harshman et al. |
| 2017/0071687 A1 | 3/2017 | Cohen et al. |
| 2017/0071688 A1 | 3/2017 | Cohen et al. |
| 2017/0095299 A1 | 4/2017 | Hendrick et al. |
| 2017/0112581 A1 | 4/2017 | Cohen et al. |
| 2017/0112583 A1 | 4/2017 | Cohen et al. |
| 2017/0119483 A1 | 5/2017 | Cohen et al. |
| 2017/0135776 A1 | 5/2017 | Cohen et al. |
| 2017/0165002 A1 | 6/2017 | Sharma et al. |
| 2017/0231701 A1 | 8/2017 | Cohen et al. |
| 2017/0239005 A1 | 8/2017 | Cohen et al. |
| 2017/0258538 A1 | 9/2017 | Cohen et al. |
| 2017/0258539 A1 | 9/2017 | Cohen et al. |
| 2017/0273702 A1 | 9/2017 | Dewaele et al. |
| 2017/0274533 A1 | 9/2017 | Berghofer et al. |
| 2017/0296170 A1 | 10/2017 | Shelton, IV et al. |
| 2018/0256235 A1 | 9/2018 | Cohen et al. |
| 2018/0256241 A1 | 9/2018 | Cohen et al. |
| 2018/0256246 A1 | 9/2018 | Cohen et al. |
| 2018/0256265 A1 | 9/2018 | Cohen et al. |
| 2018/0256266 A1 | 9/2018 | Cohen et al. |
| 2018/0256267 A1 | 9/2018 | Cohen et al. |
| 2018/0256268 A1 | 9/2018 | Cohen et al. |
| 2019/0000574 A1 | 1/2019 | Cohen et al. |
| 2019/0059868 A1 | 2/2019 | Cohen et al. |
| 2019/0059939 A1 | 2/2019 | Cohen et al. |
| 2019/0059940 A1 | 2/2019 | Cohen et al. |
| 2019/0059941 A1 | 2/2019 | Cohen et al. |
| 2019/0083193 A1 | 3/2019 | Cohen et al. |
| 2019/0167363 A1 | 6/2019 | Cohen et al. |
| 2019/0167364 A1 | 6/2019 | Cohen et al. |
| 2019/0231445 A1 | 8/2019 | Cohen et al. |
| 2020/0289225 A1 | 9/2020 | Cohen et al. |
| 2021/0059716 A1 | 3/2021 | Cohen et al. |
| 2021/0196407 A1 | 7/2021 | Cohen et al. |

(56) References Cited

U.S. PATENT DOCUMENTS

| | | |
|---|---|---|
| 2021/0236234 A1 | 8/2021 | Cohen et al. |
| 2021/0338345 A1 | 11/2021 | Cohen et al. |
| 2022/0054205 A1 | 2/2022 | Cohen et al. |

FOREIGN PATENT DOCUMENTS

| | | |
|---|---|---|
| JP | 2006-516910 | 7/2006 |
| JP | 2007-509698 | 4/2007 |
| JP | 2013-126464 | 6/2013 |
| WO | 88/04544 | 6/1988 |
| WO | 2010/096580 | 8/2010 |
| WO | 2013/116869 | 8/2013 |
| WO | 2015/019675 | 2/2015 |
| WO | 2016/035084 | 3/2016 |
| WO | 2016/035086 | 3/2016 |
| WO | 2016/035085 | 8/2016 |
| WO | 2017/037723 | 3/2017 |

OTHER PUBLICATIONS

Official Action dated Feb. 20, 2020 From the US Patent and Trademark Office Re. U.S. Appl. No. 15/358,331. (33 pages).
Notification of Office Action and Search Report dated Dec. 2, 2019 From the State Intellectual Property Office of the People's Republic of China Re. Application No. 201580052098.8 and its Summary in English.
Summons to Attend Oral Proceedings Pursuant to Rule 115(1) EPC dated Dec. 2, 2019 From the European Patent Office Re. Application No. 15838758.9. (14 Pages).
Summons to Attend Oral Proceedings Pursuant to Rule 115(1) EPC dated Nov. 19, 2019 Fromthe European Patent Office Re. Application No. 17160061.2. (6 Pages).
CN101040773 Machine Translation (by google translate)—published Sep. 26, 2007.
Summons to Attend Oral Proceedings Pursuant to Rule 115(1) EPC dated Sep. 16, 2019 From the European Patent Office Re. Application No. 15838758.9. (14 Pages).
Summons to Attend Oral Proceedings Pursuant to Rule 115(1) EPC dated Sep. 27, 2019 From the European Patent Office Re. Application No. 17160061.2. (8 Pages).
Examiners Answer dated Sep. 9, 2019 Before The Patent Trial and Appeal Board of the US Patent and Trademark Office Re. U.S. Appl. No. 15/312,732. (12 pages).
Official Action dated Aug. 7, 2019 From the US Patent and Trademark Office Re. U.S. Appl. No. 15/358,331.
Notice of Reasons for Rejection dated Jul. 2, 2019 From the Japan Patent Office Re. Application No. 2017-532229 and its Translation Into English.
Notice of Allowance dated Jul. 3, 2019 From the US Patent and Trademark Office Re U.S. Appl. No. 16/271,922.
CN102465957 Machine Translation (by google translate)—published May 23, 2012.
JP2006-516910 Machine Translation (by google translate)—published Jul. 13, 2006.
JP2007-509698 Machine Translation (by google translate)—published Apr. 19, 2007.
JP2013-126464 Machine Translation (by google translate)—published Jun. 27, 2013.
Application-Initiated Interview Summary dated May 31, 2019 From the US Patent and Trademark Office Re. U.S. Appl. No. 16/271,915.
Advisory Action Before the Filing of An Appeal Brief dated May 21, 2019 From the US Patent and Trademark Office Re. U.S. Appl. No. 15/312,732.
Summons to Attend Oral Proceedings Pursuant to Rule 115(1) EPC and Communication From the Examining Division dated May 14, 2019 From the European Patent Office Re Application No. 16840991.0.
Applicant-Initiated Interview Summary dated Apr. 24, 2019 From the US Patent and Trademark Office Re. U.S. Appl. No. 15/358,331.
Advisory Action Before the Filing of an Appeal Brief dated Feb. 13, 2019 From the US Patent and Trademark Office Re. U.S. Appl. No. 15/454,116.
Advisory Action Before the Filing of an Appeal Brief dated Jan. 24, 2019 From the US Patent and Trademark Office Re. U.S. Appl. No. 15/454,116.
Communication Pursuant to Article 94(3) EPC dated Mar. 4, 2019 From the European Patent Office Re. Application No. 15838758.9.
Communication Pursuant to Article 94(3) EPC dated Apr. 8, 2019 From the European Patent Office Re. Application No. 15838126.9.
Communication Pursuant to Article 94(3) EPC dated Mar. 11, 2019 From the European Patent Office Re. Application No. 17160061.2.
Official Action dated Apr. 4, 2019 From the US Patent and Trademark Office Re. U.S. Appl. No. 16/271,915.
Official Action dated Mar. 22, 2019 From the US Patent and Trademark Office Re. U.S. Appl. No. 15/454,123.
Official Action dated Jan. 9, 2019 From the US Patent and Trademark Office Re. U.S. Appl. No. 15/358,331.
Official Action dated Dec. 14, 2018 From the US Patent and Trademark Office Re. U.S. Appl. No. 15/454,116.
Official Action dated Nov. 14, 2018 From the US Patent and Trademark Office Re. U.S. Appl. No. 15/312,732.
Official Action dated Jul. 23, 2018 From the US Patent and Trademark Office Re. U.S. Appl. No. 15/924,635.
Advisory Action Before the Filing of an Appeal Brief dated Jul. 13, 2018 From the US Patent and Trademark Office Re. U.S. Appl. No. 15/454,123.
Supplementary European Search Report and the European Search Opinion dated Jun. 21, 2018 From the European Patent Office Re. Application No. 16840991.0.
Official Action dated Jun. 28, 2018 From the US Patent and Trademark Office Re. U.S. Appl. No. 15/454,116.
Official Action dated Jun. 29, 2018 From the US Patent and Trademark Office Re. U.S. Appl. No. 15/312,732.
Supplementary European Search Report and the European Search Opinion dated Jun. 11, 2018 From the European Patent Office Re. Application No. 15838126.9.
Ramos et al. "Human Hybrid Notes Transvaginal Sleeve Gastrectomy: Initial Experience", Surgery for Obesity and Related Diseases, 4: 660-663, 2008.
Notice of Allowance dated Apr. 13, 2018 From the US Patent and Trademark Office Re. U.S. Appl. No. 15/402,257.
Supplementary European Search Report and the European Search Opinion dated Apr. 2, 39018 From the European Patent Office Re. Application No. 15838758.9.
Official Action dated Mar. 20, 2018 From the US Patent and Trademark Office Re. U.S. Appl. No. 15/454,123.
International Preliminary Report on Patentability dated Mar. 15, 2018 From the International Bureau of WIPO Re. Application No. PCT/IL2015/050892.
Official Action dated Feb. 28, 2018 From the US Patent and Trademark Office Re. U.S. Appl. No. 15/358,331.
Applicant-Initiated Interview Summary dated Mar. 7, 2018 From the US Patent and Trademark Office Re. U.S. Appl. No. 15/312,732.
Restriction Official Action dated Feb. 7, 2018 From the US Patent and Trademark Office Re. U.S. Appl. No. 15/454,116.
Applicant-Initiated Interview Summary dated Jan. 26, 2018 From the US Patent and Trademark Office Re. U.S. Appl. No. 15/418,891.
Official Action dated Jan. 26, 2018 From the US Patent and Trademark Office Re. U.S. Appl. No. 15/312,732.
Official Action dated Dec. 13, 2017 From the US Patent and Trademark Office Re. U.S. Appl. No. 15/402,257.
Official Action dated Dec. 4, 2017 From the US Patent and Trademark Office Re. U.S. Appl. No. 15/358,325.
Official Action dated Nov. 27, 2017 From the US Patent and Trademark Office Re. U.S. Appl. No. 15/418,891.
Applicant-Initiated Interview Summary dated Oct. 6, 2017 From the US Patent and Trademark Office Re. U.S. Appl. No. 15/454,123.
Applicant-Initiated Interview Summary dated Oct. 2, 2017 From the US Patent and Trademark Office Re. U.S. Appl. No. 15/358,331.
European Search Report and the European Search Opinion dated Aug. 22, 2017 From the European Patent Office Re. Application No. 17160061.2.

(56) References Cited

OTHER PUBLICATIONS

Official Action dated Aug. 28, 2017 From the US Patent and Trademark Office Re. U.S. Appl. No. 15/454,123.
Official Action dated Aug. 7, 2017 From the US Patent and Trademark Office Re. U.S. Appl. No. 15/358,325.
Applicant-Initiated Interview Summary dated Jul. 19, 2017 From the US Patent and Trademark Office Re. U.S. Appl. No. 15/418,891.
Official Action dated Jul. 10, 2017 From the US Patent and Trademark Office Re. U.S. Appl. No. 15/358,331.
Official Action dated Jun. 5, 2017 From the US Patent and Trademark Office Re. U.S. Appl. No. 15/418,891.
International Preliminary Report on Patentability dated Mar. 16, 2017 From the International Bureau of WIPO Re. Application No. PCT/IL2015/050892.
International Preliminary Report on Patentability dated Mar. 16, 2017 From the International Bureau of WIPO Re. Application No. PCT/IL2015/050891.
International Preliminary Report on Patentability dated Mar. 16, 2017 From the International Bureau of WIPO Re. Application No. PCT/IL2015/050893.
Restriction Official Action dated Mar. 17, 2017 From the US Patent and Trademark Office Re. U.S. Appl. No. 15/418,891.
Official Action dated Mar. 9, 2017 From the US Patent and Trademark Office Re. U.S. Appl. No. 15/401,045.
Official Action dated Mar. 10, 2017 From the US Patent and Trademark Office Re. U.S. Appl. No. 15/402,342.
International Search Report and the Written Opinion dated Mar. 24, 2016 From the International Searching Authority Re. Application No. PCT/IL2015/050893.
International Search Report and the Written Opinion dated Mar. 11, 2016 From the International Searching Authority Re. Application No. PCT/IL2015/050892.
International Search Report and the Written Opinion dated Feb. 26, 2016 From the International Searching Authority Re. Application No. PCT/IL2015/050891.
Invitation to Pay Additional Fees dated Dec. 3, 2015 From the International Searching Authority Re. Application No. PCT/IL2015/050891.
Invitation to Pay Additional Fees dated Jan. 12, 2016 From the International Searching Authority Re. Application No. PCT/IL2015/050893.
Box et al. "Rapid Communciation: Robot-Assisted Notes Nephrectomy: Initial Report", Journal of Endourology, 22(3): 503-506, Mar. 2008. Abstract.
Domingo et al. "Overview of Current Trends in Hysterectomy", Expert Reviews of Obstetrics & Gynaecology, 4(6): 673-685, 2009.
Hubens et al. "What Have We Learnt After Two Years Working With the Da Vinci Robot System in Digestive Surgery?", Acta Chirurgica Belgica, 104(6): 609-614, Nov.-Dec. 2004.
Irvine et al. "Anaesthesia for Robot-Assisted Laporoscopic Surgery", Continuing Education in Anaesthesia, Critical Care & Pain, 9(4): 125-129, Advance Access Published Jun. 25, 2009.
Kho et al. "Vaginal Versus Laparoscopic Hysterectomy. Vaginal Hysterectomy: The Best Minimally Invasive Approach", Contemporary OB/GYNObstetrics & Women's Health, 7 P., Oct. 1, 2013.
Komura et al. "An Inverse Kinematics Method for 3D Figures With Motion Data", Proceedings of the Computer Graphics International, CGI'03, Jul. 9-11, 2003, p. 266-271, Jul. 2003.
Lee "Anesthetic Considerations for Robotic Surgery", Korean Journal of Anesthesiology, 66(1): 3-11, Jan. 2014.
Piccigallo et al. "Design of a Novel Bimanual Robotic System for Single-Port Laparoscopy", IEEE/ASME Transactions on Mechatronics, 15(6): 871-878, Dec. 13, 2010.
Teljeur et al. "Economic Evaluation of Robot-Assisted Hysterectomy: A Cost-Minimisation Analysis", BJOG: An International Journal of Obstetrics and Gynaecology, 121(12): 1546-1555, Published Online May 9, 2014.
International Search Report and the Written Opinion dated Dec. 5, 2016 From the International Searching Authority Re. Application No. PCT/IL2016/050976.

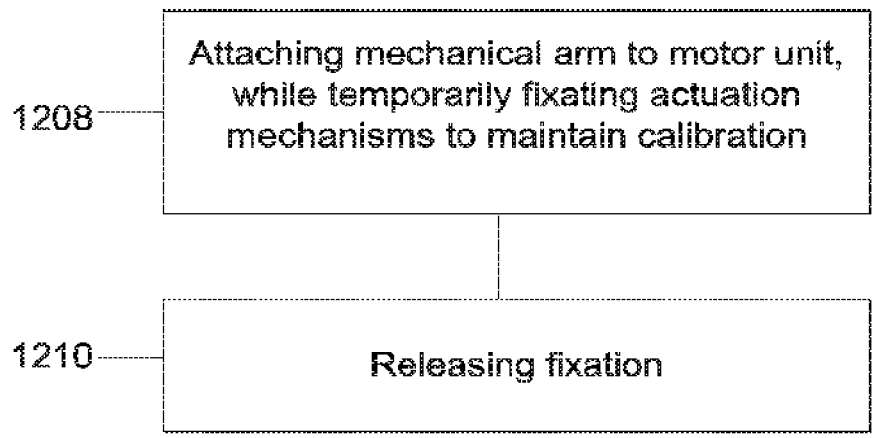
FIGURE 12A
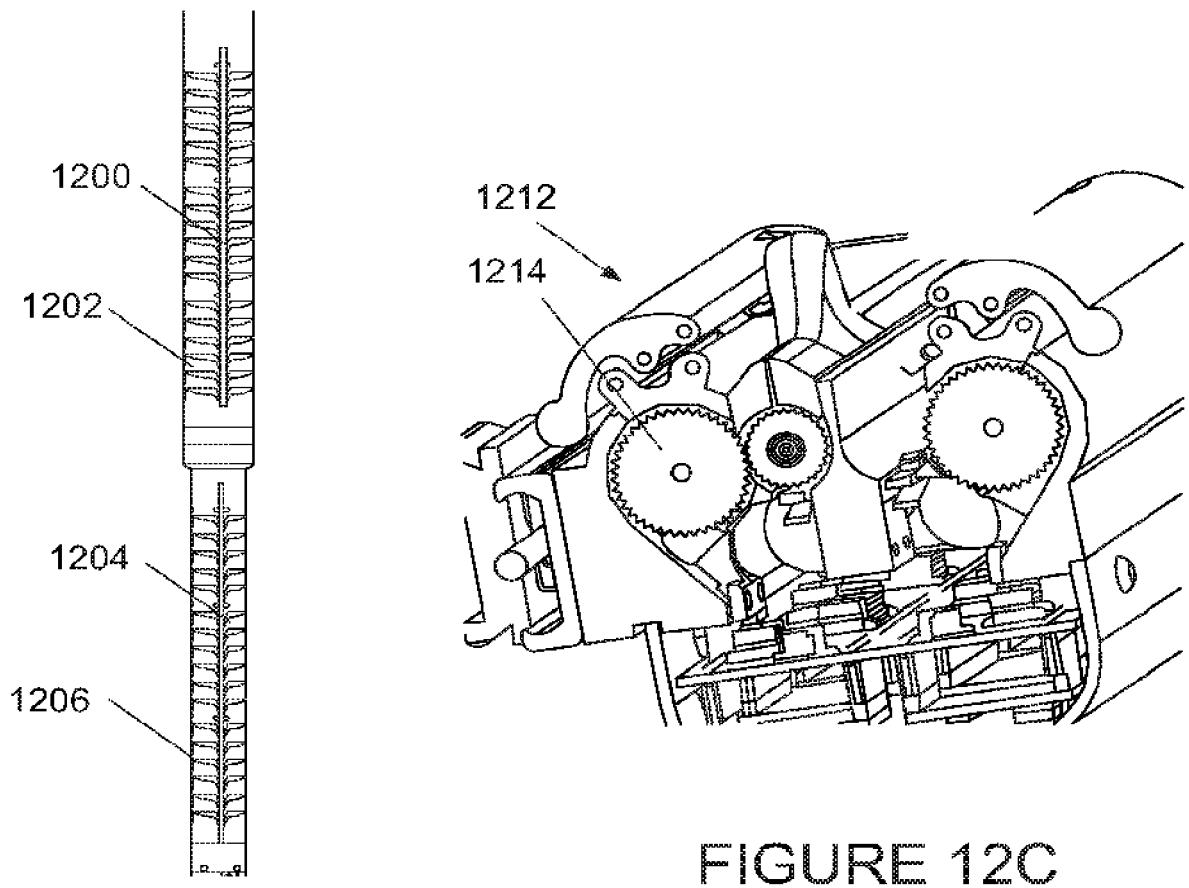
FIGURE 12B
FIGURE 12C

ACTUATION OF A DEVICE COMPRISING MECHANICAL ARMS

RELATED APPLICATION

This application is related to PCT Patent Application No. PCT/IL2015/050893 filed on Sep. 4, 2015, the contents of which are incorporated by reference as if fully set forth herein in their entirety. This application is related to PCT Patent Application No. PCT/IL2016/050976 filed on Sep. 4, 2016, the contents of which are incorporated by reference as if fully set forth herein in their entirety.

FIELD AND BACKGROUND OF THE INVENTION

The present invention, in some embodiments thereof, relates to actuation of a device including at least one surgical arm and, more particularly, but not exclusively, to a motor unit configured for actuating at least one surgical arm.

Background art includes: "Design of a Compact Robotic Manipulator for Single-Port Laparoscopy" by Claudio Quaglia et al, Paper No: MD-13-1148 in J. Mech. Des. 136(9), 095001 (Jun. 13, 2014); "An inverse kinematics method for 3D figures with motion data" by Taku Komura et al., Proceedings of the Computer Graphics International (CGI'03);

Hubens et al., 2004, "What Have we Learnt after Two Years Working with the Da Vinci Robot System in Digestive Surgery?", Acta chir belg;

Michael Irvine, 2009, "Anaesthesia for Robot-Assisted Laparoscopic Surgery", Cont Edu Anaesth Crit Care and Pain;

Jeong Rim Lee, 2014, "Anesthetic considerations for robotic surgery", Korean Journal of Anesthesiology;

Teljeur et al., 2014, "Economic evaluation of robot-assisted hysterectomy: a cost-minimisation analysis", BJOG;

Box et al., 2008, "Rapid communication: robot-assisted NOTES nephrectomy: initial report", J Endourol; DR. Domigo, 2009, "Overview of current hysterectomy trends", Expert Review of Obstetrics & Gynecology; and DR. Kho, "Vaginal versus laparoscopic hysterectomy", Contemporary OB/GYN Expert Advice, 2013.

Additional background art includes U.S. Pat. Nos. 8,224,485, 8,347,754, 7,833,156, 8,518,024, International Patent Application Publication No. WO 2010096580, and International Patent Application Publication No. WO 2013116869.

SUMMARY OF THE INVENTION

According to an aspect of some embodiments of the invention, there is provided a mechanism for actuating movement of a shaft having two degrees of freedom, comprising: a first actuator configured to rotate the shaft around the shaft axis; a second actuator configured to bend the shaft using one or more elongated elements attached to the shaft; wherein actuation of the first actuator indirectly manipulates the elongated elements controlled by the second actuator, thereby affecting operation of the second actuator.

In some embodiments, the mechanism comprises at least one motor and at least one of the first and second actuators comprises at least one gear driven by the motor.

In some embodiments, the indirect manipulation comprises changing a position of the elongated elements in response to rotation of the shaft by the first actuator.

In some embodiments, rotation of the shaft by the first actuator tensions at least one of the elongated elements controlled by the second actuator.

In some embodiments, the elongated elements are attached to the shaft at a point distal to a flexible joint of the shaft.

In some embodiments, the second actuator is configured to respectively tension and releases the elongated elements to cause flexion and extension of the joint.

In some embodiments, one or both of the first and second actuators comprises a gear.

In some embodiments, the gear is positioned to rotate about the shaft axis.

In some embodiments, both of the actuators comprise gears and are positioned to rotate about the shaft axis.

In some embodiments, relative actuation of the first and second actuators is configured to bend the shaft.

In some embodiments, the relative actuation comprises driving the actuators at different speeds.

In some embodiments, unified actuation of the first and second actuators is configured to rotate the shaft as a single rigid body.

In some embodiments, each of the actuators is driven by a motor.

In some embodiments, a gear of the motor or one or more transmission gears driven by the motor are positioned to interfere, at least in part, with rotation of the second actuator.

In some embodiments, an amount of friction imposed on the second actuator by the interference effects a final shaft articulation actuated by the mechanism.

In some embodiments, when high friction is imposed on the second actuator, actuation of the first actuator results in simultaneous rotation and bending of the shaft; and when low or no friction is imposed on the second actuator, actuation of the first actuator results in rotation of the shaft as a rigid body.

In some embodiments, the shaft forms at least a portion of a surgical arm.

According to an aspect of some embodiments of the invention, there is provided a surgical system comprising a surgical arm comprising at least one joint; a motor unit configured to actuate articulation of the at least one joint of the surgical arm, the motor unit comprising a proximal extension of the arm; wherein the motor unit comprises at least one actuation mechanism configured for one or both of rotating at least a portion of the arm around its axis and bending the at least one joint, the actuation mechanism operably coupled to the extension of the arm.

In some embodiments, the portion of the arm which is moved by the actuation mechanism is configured proximally to the joint.

In some embodiments, the arm comprises at least one inner shaft nested within an outer shaft, the inner and outer shafts extending in a proximal direction and forming the proximal extension of the arm.

In some embodiments, the actuation mechanism comprises a first proximal gear and a second distal gear; wherein the outer shaft is operably coupled to the distal gear, and the inner nested shaft extends in a proximal direction to and through the proximal gear.

In some embodiments, each of the gears is driven directly or via a gear transmission by a motor.

In some embodiments, the arm comprises 3 joints actuated by 3 actuation mechanisms.

In some embodiments, more than one actuation mechanism is actuated to generate a selected articulation of the arm.

In some embodiments, articulation of the outer shaft is performed concurrently with articulation of the inner shaft.

In some embodiments, the actuation mechanisms are collinear.

In some embodiments, the system comprises two surgical arms and the motor unit comprises actuations mechanisms for articulating both arms.

In some embodiments, the motor unit is less than 500 mm in length and less than 70 mm in width.

In some embodiments, the motor unit comprises one or more position sensors for indicating a current angular position of the motor gear.

In some embodiments, a controller of a first motor is configured to receive input from a position sensor of a second motor and to control operation of the first motor in response to the input.

According to an aspect of some embodiments of the invention, there is provided a mechanism for linear movement of elongated elements driven by rotational movement, comprising: a gear operably coupled to a threaded screw, the gear configured to rotate the screw around the screw axis; at least two rider elements coupled to the thread of the screw; wherein a first rider element is attached to at least one first elongated element and a second rider element is attached to at least one second elongated element; wherein rotation of the screw moves the rider elements laterally in opposing directions, tensioning the first elongated element and releasing tension of the second elongated element or vice versa.

In some embodiments, rotational movement of the rider elements around the screw is limited by one or more protrusions configured on an internal face of a housing in which the screw is received.

In some embodiments, a coupling between the gear and the screw comprises a clutch. In some embodiments, the clutch comprises a spring coupled to the screw such that when torque and/or tension produced by rotation of the screw exceeds a threshold, the spring yields and further rotation of the screw is no longer effective to actuate movement of the elongated elements.

In some embodiments, the clutch comprises one or more springs attached between the rider elements and the elongated elements such that when an elongated element is tensioned above a threshold, the spring yields and further movement of the rider element is no longer effective to tension the elongate element.

In some embodiments, each of the rider elements is attached to two elongated elements.

In some embodiments, the elongated elements are each coupled at their proximal end to the respective rider element, and at their distal end to a shaft which forms at least a portion of a surgical arm.

In some embodiments, the elongated elements are coupled to the shaft at a point distal to a flexible joint of the shaft.

According to an aspect of some embodiments of the invention, there is provided a mechanism for actuating a shaft having two degrees of freedom, comprising: a tubular shaft; first and second actuators disposed at an end of the tubular shaft, the actuators collinear to the tubular shaft; wherein the first actuator is configured to actuate shaft movement of a first type, and the second actuator is configured to actuate shaft movement of a second type, the movement of a second type different than the movement of a first type.

In some embodiments, one or both of the first and second actuators comprises a gear.

In some embodiments, the first and second actuators are configured to move about a central axis of the tubular shaft.

In some embodiments, the first and second actuators are spaced apart from each other.

In some embodiments, the first actuator is directly coupled to the tubular shaft and the second actuator is indirectly coupled to the tubular shaft.

In some embodiments, the second actuator is coupled to the tubular shaft via one or more elongated elements extending between the second actuator and the tubular shaft.

In some embodiments, movement of a first type comprises rotation of the tubular shaft around its axis and movement of a second type comprises bending of the tubular shaft.

According to an aspect of some embodiments of the invention, there is provided a method of maintaining calibration of a surgical arm, comprising positioning an extension of a surgical arm in a motor unit configured to actuate articulation of the surgical arm by comprising one or more gears operably coupled to the extension; during positioning, interfering with movement of the one or more gears to maintain a calibrated state of the surgical arm.

In some embodiments, interfering comprises changing a position of interfering elements to a gear-locking position using an elastic element.

In some embodiments, the method further comprises closing a cover door of the motor unit to release the interfering elements from the gear-locking position.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 8c is a cross-section view taken along a plane perpendicular to the longitudinal axis of the assembly shown in the figure. In contrast, FIG. 8A is not a section view;

FIG. 12A is a flowchart of a method for maintaining calibration of a surgical arm, according to some embodiments of the invention;

FIG. 12B illustrates a calibrated position of a surgical arm, according to some embodiments of the invention;

FIG. 12C is a cross section of the motor unit including a surgical arm (or extension thereof) received within the motor unit, according to some embodiments of the invention;

DESCRIPTION OF SPECIFIC EMBODIMENTS OF THE INVENTION

Figure 1A:
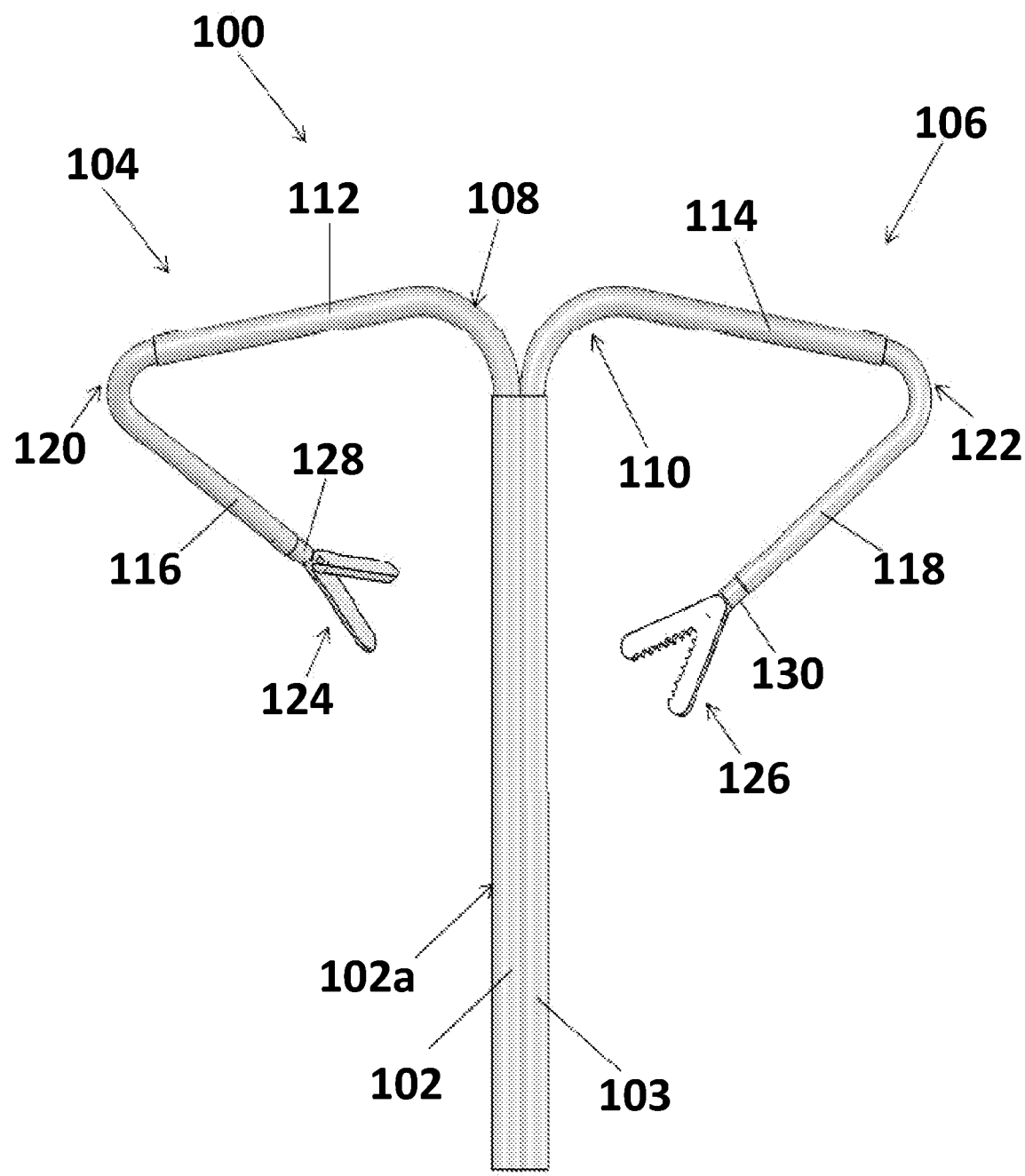
FIG. 1A is a simplified schematic side view of a surgical device including a plurality of arms, according to some embodiments of the invention.

The present invention, in some embodiments thereof, relates to actuation of a device including at least one surgical arm and, more particularly, but not exclusively, to a motor unit configured for actuating at least one surgical arm.

A broad aspect of some embodiments relates to actuation of a surgical arm, and more particularly, but not exclusively, to motorized actuation of a surgical arm.

An aspect of some embodiments relates to actuating movement of a shaft (e.g. a segment of the surgical arm) having two degrees of freedom using two actuators configured to interact with each other such that actuation of the first actuator indirectly manipulates one or more elongated elements attached to the shaft and controlled by the second actuator. In some embodiments, indirect manipulation comprises rotating the shaft, causing a change in a position of the elongated elements attached to the shaft.

In some embodiments, the first actuator is configured to rotate the shaft around the shaft axis. In some embodiments, the second actuator is configured to bend the shaft, for example by relative tensioning and releasing of the elongated elements attached to the shaft, for example attached at a point distal to a flexible portion of the shaft. In some embodiments, rotation of the shaft by the first actuator tensions the elongated elements, thereby affecting operation of the second actuator, which controls the elongated elements. In some embodiments, the first actuator is located between the second actuator and the attachment point of the elongated elements to the shaft, such that the elongated elements extend past the first actuator (e.g. pass from proximally to the first actuator to distally of the first actuator).

In some embodiments, the actuator comprises a gear or a gear train. In some embodiments, relative actuation of the actuators, comprising, for example, rotating the gears at different speeds and/or directions, holding one gear stationary whilst the other gear is rotated is configured to actuate a first type of movement the shaft, for example bending of the shaft. In some embodiments, unified actuation of the actuators, comprising, for example, rotating the gears at similar speeds, is configured to actuate a second type of movement of the shaft, for example rotation of the shaft as a single rigid body.

In some embodiments, one or more elements such as a gear of a motor driving the actuator are configured to interfere with free rotation of the actuator. In some embodiments, an amount of resistance imposed on the second actuator (e.g. friction due to the interfering motor gear) during actuation of the first actuator affects the type of movement produced by actuation of the first actuator. For example, if the resistance is high enough to hold the second actuator stationary whilst the first actuator is rotated, actuation of the first actuator will result in simultaneous rotation and bending of the shaft. Alternatively, if low or no friction is encountered by the second actuator, rotation of the first actuator will in turn rotate the second actuator, resulting in rotation of the controlled shaft as a single rigid body.

In some embodiments, a threshold is applied for actuating a selected movement of the shaft, for example, the gears need to be rotated at a selected minimal speed in order to rotate the shaft as a rigid, single body.

An aspect of some embodiments relates to a shaft actuation mechanism comprising two or more actuators movable about a similar rotational axis. In some embodiments, the rotational axis is the same as the rotational axis of the shaft. In some embodiments, at least one of the actuators is configured to rotate the shaft about the common rotational axis. Optionally at least one other actuator is configured to produce bending of the shaft and/or linear movement of the shaft.

An aspect of some embodiments relates to articulating a plurality of shafts that are nested, at least in part, within one another. In some embodiments, articulation of an outer shaft requires simultaneous articulation of an inner shaft positioned within the outer shaft. In an example, in order to bend an outer shaft, an inner shaft nested at least in part within the outer shaft is bent as well.

Some embodiments relate to a system comprising a motor unit configured for actuating movement of a surgical arm including a plurality of nested shafts. In some embodiments, the motor unit comprises one more actuation mechanisms, configured for articulating (e.g. bending and/or rotating) at least a segment of the surgical arm. As referred to herein, an "actuation mechanism" may include one or more actuators, such as gear or gear trains, configured for actuating movement of a joint of the surgical arm. In some embodiments, the actuation mechanism is configured for rotating an arm segment proximal to the joint around the segment's long axis, as well as bending (flexing and/or extending) the joint. In an embodiment, an actuation mechanism comprises a rotation gear configured at a distal end of the mechanism, and a bending gear configured at a proximal end of the actuation mechanism. In some embodiments, an outer shaft is operably attached to the rotation gear such that the rotation gear is configured to rotate the outer shaft around the shaft long axis. In some embodiments, an inner shaft nested within the outer shaft extends in a proximal direction to and through the bending gear, optionally continuing in the proximal direction to be operably received within a second actuation mechanism, and so forth.

In some embodiments, the bending and rotation gear are driven in different manners, for example, in some embodiments, the bending gear is rotated by a second gear driven by a motor, while the rotation gear is directly driven by a motor. Additionally or alternatively, gears of different shapes and/or sizes (e.g. having different number of teeth) are used to drive the movement actuating gears. A potential advantage of using a gear train and/or gears of different sizes may include reducing a speed of the driving motor, increasing torque and allowing for a higher degree of accuracy in control of arm movements. Additionally or alternatively, a selectable gear configured for modifying the motor speed to a selected speed is used.

In some embodiments, a certain actuation speed is selected. In some embodiments, the speed is selected in accordance with a surgical action performed by the arm, for example performed by an end-effecter at a distal end of the arm. For example, in some embodiments, for actuation of an end-effecter of the arm such as grippers configured at a distal end of the arm, when actuating fast gripper movement, e.g. during tissue dissection, a high speed is selected; when actuating gripper movement which requires a relatively high amount of force to applied by the gripper, for example when stapling tissue, separating tissue and/or other actions associated with applying of a relatively high amount of force via the grippers, a slower motor speed is selected. In some embodiments, articulation of a joint of the surgical arm involves actuating different combinations of actuators, for example, rotation of an elbow joint is obtained by a combination of 4 actuators, while flexion of the elbow joint is obtained by a single actuator. In some embodiments, articulation of two or more joints is performed concurrently, for example, when bending the shoulder, bending of the elbow is actuated as well so as not to limit bending of the shoulder.

In some embodiments, articulation is performed in accordance with a current position of the surgical arm. Optionally, the motor unit comprises position sensors and/or is controlled by a processor, optionally including a memory which stores commands. In some embodiments, data from position sensor/s and/or from control memory is used to infer a position of the arm portion(s). In some embodiments, the processor receives signals from an input device (e.g. a joystick) and/or from a user motion detector device, and controls activation of the motor unit based on the received signals.

In some embodiments, a long axis of the motor unit is collinear with the long axis of the surgical arm. In some embodiments, the plurality of actuation mechanisms of the motor unit are aligned concentrically with respect to each other, and/or with respect to the arm. In some embodiments, the prime actuators (e.g. motors) are shaped and sized to be disposed in parallel to the actuation mechanism, optionally beside and/or beneath the actuation mechanism, to allow for a thin motor unit.

In some embodiments, the motor unit comprises a mirrored arrangement of actuations mechanisms for actuating two surgical arms (optionally imitating left and right human arms). Alternatively, the motor unit is configured for actuating a single arm. In some embodiments, a motor unit comprising 3 actuation mechanisms, optionally driven by 6 motors, is configured to actuate a single arm, for example an arm comprising 3 joints.

In some embodiments, the motor unit is of small dimensions, for example a motor unit configured for actuating two arms comprises a width of less than 60 mm, less than 70 mm, less than 90 mm or intermediate, larger or smaller size, and/or a length of less than 300 mm, less than 400 mm, less than 500 mm or intermediate, larger or smaller size. In some embodiments, during use, at least a portion of the surgical arm(s) is inserted into the body (through a natural body orifice and/or through an incised port), while the motor unit remains outside the body. Alternatively, the motor unit is small enough to be inserted, at least in part, into the body.

An aspect of some embodiments relates to actuating linear movement driven by rotational movement. In some embodiments, a threaded screw is configured to be rotated about its axis, for example by a gear (e.g. a bending gear for example as described hereinabove), causing lateral movement of one or more rider elements, such as half-nuts, that fit within the grooves defined by the thread and/or fit within indentations defined by radially-inward protrusions on the housing. In some embodiments, two half nuts are used, each of the half-nuts being coupled to an elongate element, so that rotation of the screw causes one half nut to move distally and the other half nut to move proximally, thereby causing respective tensioning and releasing of the elongated elements. In some embodiments, a distal end of the elongated elements is attached to a bendable shaft at a point distal to a flexible portion defining a joint, and bending of the shaft is achieved by relative flexion and extension actuated by the linearly moved elongated elements.

In some embodiments, a coupling between the rotation gear and the threaded screw comprises a clutch. In some embodiments, the clutch comprises an elastic element such as a spring (e.g. a torsion and/or tension spring) which is coupled to the threaded screw, optionally at a distal end of the screw. Optionally, when torque and/or tension applied by the rotated screw to the spring exceeds a certain threshold, the spring yields and further rotation of the screw is no longer effective to move the elongated elements. Additionally or alternatively, the clutch comprises a spring disposed at the attachment between the elongate element and the half nut. Optionally, when a pulling force applied to the elongated element via the spring exceeds a certain threshold, the spring yields and further rotation of the screw is no longer effective to move the elongated elements. In some embodiments, the clutch is operably coupled to an encoder configured to send a signal to a driver circuit controlling a motor actuating the rotation gear, for example so that the motor is stopped in response to the signal.

An aspect of some embodiments relates to temporarily fixating a surgical arm at a selected position, for example maintaining a calibrated state of the surgical arm during attachment of the arm to a motor unit. In some embodiments, movement of one or more movement actuating gears (e.g. bending and/or rotation gears) is limited or prevented, for example by elements configured to interfere with movement of the gear. In some embodiments, completion of the attachment process such as by closing a cover door of the motor unit releases the interfering elements, allowing the gears to rotate again.

An aspect of some embodiments relates to safety of a device comprising one or more surgical arms. In some embodiments, the motor unit comprises one or more mechanisms for reducing risk during a power outage, for example: a solenoid lock which locks a cover of the motor unit during power outage; a manual mode in which the motor unit can be operated manually, for example by the surgeon; and/or other mechanisms configured for limiting manipulation of the arm and/or for limiting user access, for example during power outage.

In some embodiments, the motor unit comprise one or more mechanisms for reducing risk of human error during operation, for example, a relay that prevents power delivery to an electrocautery instrument when the instrument is mistakenly attached to the wrong device arm (e.g. in a device comprising two arms, the electrocautery instrument being attached to the arm defined as the left arm instead of the arm defined as the right arm or vice versa).

In some embodiments, the motor unit comprises one or more mechanisms for self-controlled operation, for example: cross-control of the motors in which a safety sensor of a first motor is controlled by a driver circuit controlling a second motor; selective delivery of monopolar or bipolar energy to the end effecter using, for example, a slip ring, and/or other energy delivery control mechanisms.

In some embodiments, mechanisms and/or systems and/or methods for example as described herein are used in robot-assisted surgeries and/or computer assisted surgeries. Robot-assisted surgeries may include, for example, minimally invasive surgeries (e.g. surgeries in which a less than 5 cm incision is made, a less than 2 cm incision is made, a less than 1 cm incision or intermediate, larger or smaller incision is made); open surgical procedures; single port procedures; multi-port procedures and/or other types of surgeries.

In some embodiments, mechanisms and/or systems for example as described herein are configured to be controlled remotely. In some embodiments, the robot (comprising the one or more surgical arms for example as described herein) is positioned on and/or below and/or otherwise adjacent the operating table. In some embodiments, control of the one or more surgical arms for example as described herein (e.g. arms as shown in FIGS. 1A-D and/or FIG. 2 and/or FIGS. 4A-C and/or FIG. 5 and/or FIG. 6A and/or other figures described), is provided via a console which may be located in the operating room, optionally adjacent the operating table and the surgical arms. Additionally or alternatively, control of the one or more surgical arms is performed from a distance.

A "robot" as referred to herein may include, in accordance with some embodiments, an electromechanical machine comprising one more surgical arms for example as described herein, which are controlled by circuitry, for example controlled by a computer. In some embodiments, movement of the at least one surgical arm such as rotation of at least a portion of the arm; bending of the arm; axial movement of the arm (e.g. back and forth movement of the arm) and/or or other movements and/or articulations for example as described herein are driven by one or more motors operably coupled to the surgical arm.

In some embodiments, the robot is configured to carry out movements associated with surgery, for example movements that would have been otherwise performed by a surgeon. In some embodiments, the robot is configured to control operation of surgical instruments inside and/or outside the patient body, e.g. to actuate movement of an end effecter such as a gripper.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1A is a simplified schematic side view of a device 100 (e.g. surgical device) including a plurality of arms, according to some embodiments of the invention.

In some embodiments, the device includes a first arm 104 and a second arm 102.

In some embodiments each arm 104, 106 includes a support segment 102, 103, coupled to a first segment 112, 114 by a first connecting section 108, 110, where first segment 112, 114 is coupled to a second segment 116, 118 by a second connecting section 120, 122, and a third segment 124, 126 coupled to second segment 116, 118 by a third connecting section 128, 130.

In some embodiments, one or more of support segments 102, 103 are rigid. In some embodiments one or more of support segments 102, 103 are flexible or include a flexible portion.

Figure 1B:
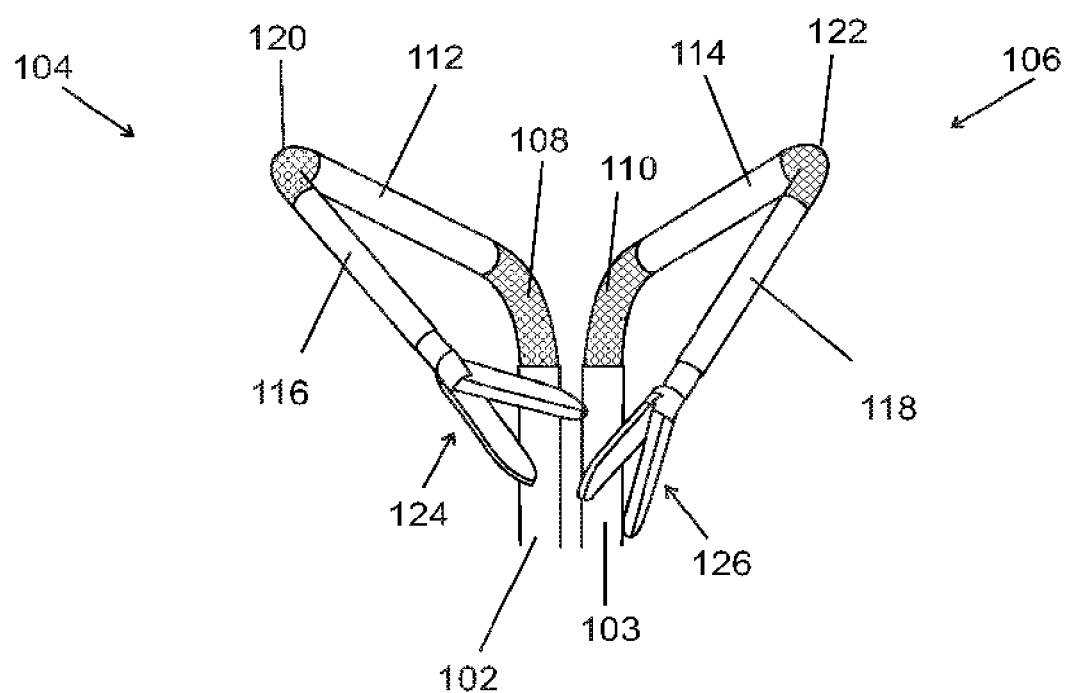
FIG. 1B is a simplified schematic of a device including a plurality of arms, according to some embodiments of the invention.

In some embodiments, support segments 102, 103 are coupled, e.g. by a cover 102a. In some embodiments, support segments are coupled at only a portion of the torso length or are not coupled: FIG. 1B is a simplified schematic of a device 100 including a plurality of arms 104, 106, according to some embodiments of the invention.

In some embodiments, one or more arm includes a humanoid like structure. For clarity, in some portions of this document, device segments and connecting sections are referred to by anatomical names: Support segments 102, 103 are also termed first torso 102 and second torso 103, first connecting sections 108, 110 are also termed first shoulder joint 108, second shoulder joint 110, first segments, 112, 114 are also termed first humerus 112 and second humerus 114, second connecting sections 120, 122 are also termed first elbow joint 120, and second elbow joint 122, second segments 116, 118 are also termed first radius 116 and second radius 118 and third segments 124 and 126 are also termed first hand tool 124 and second hand tool 126.

In some embodiments, one or more connecting section includes a hinge. In some embodiments, one or more connecting section is flexible and/or includes a flexible portion. In an exemplary embodiment, a device arm includes an elbow joint and a shoulder joint where bending of the joint is distributed along the joint in a direction of a joint long axis.

In some embodiments, torsos 102, 103 are close together, for example, a long axis of first torso 102 and a long axis of second torso 103 are within 5 mm, or 3 mm, or 1 mm of each other. Alternatively, torsos 102, 103 are spaced apart from each other. Additionally or alternatively, torsos 102, 103 are configured to converge or to diverge relative to each other. Optionally, a torso is curved.

In some embodiments, one or more device segment has a substantially cylindrical external shape (e.g. radius, humerus). In some embodiments, joints have circular long axis cross-section. Alternatively, in some embodiments, one or more device segment and/or joint has non-circular cross section external shape, for example, oval, square, rectangular, irregular shapes.

In some embodiments, a surgical arm includes one or more short and/or adjustable segment. In some embodiments, flexible portions are directly connected.

In some embodiments, a flexible portion comprises a plurality of stacked links.

Figure 1C:
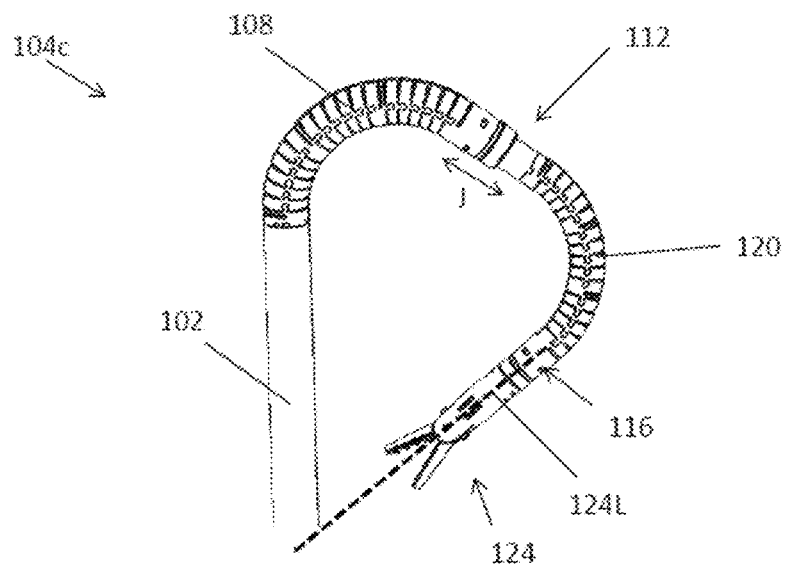
FIGS. 1C-D are simplified schematic side views of surgical arms, according to some embodiments of the invention.
Figure 1D:
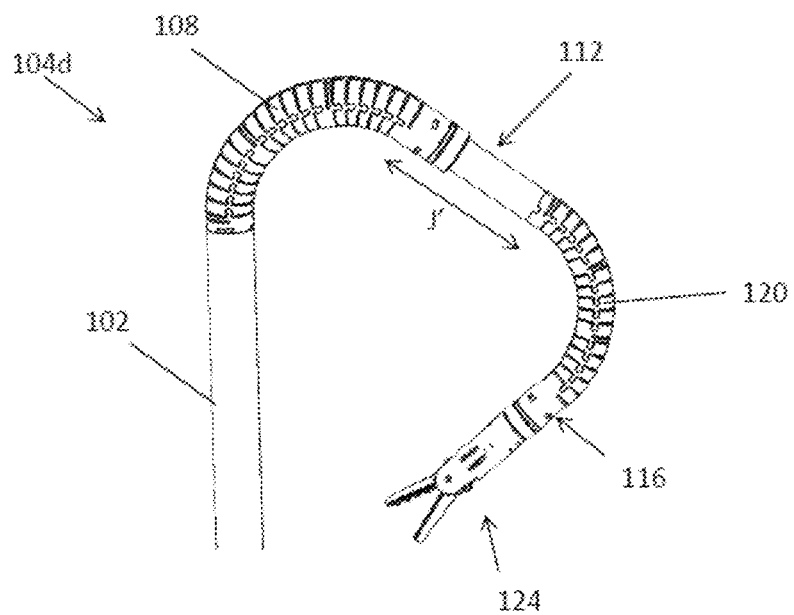

FIGS. 1C-D are simplified schematic side views of surgical arms, according to some embodiments of the invention. FIG. 1C illustrates an exemplary embodiment where a humerus segment 112 is short, for example, the segment including a long axis length, J of 1-50 mm, or 1-35 mm, or 10-20 mm, or approximately 10 mm or lower or higher or intermediate ranges or lengths.

In some embodiments, a user selects arm\s including desired segment lengths, where for example, selection is based on patient anatomy and/or a procedure to be performed. For example, when treating a child, a user, in some embodiments, selects one or more arm with one or more short segment (e.g. as illustrated by FIG. 1C). For example, when treating an obese patient, a user, in some embodiments, selects an arm with one or more a long segment for example, a standard arm with a long humerus segment (e.g. as illustrated by FIG. 1D) (e.g. humerus segment length, J' is 10-100 mm, or 20-35 mm, or 10-20 mm, or lower or higher or intermediate ranges or lengths).

In some embodiments, a device includes a kit with different structured arms (e.g. different segment lengths, e.g. different arm sizes).

Alternatively or additionally, in some embodiments, one or more segment length is adjustable, e.g. during a treatment and/or during set-up of the device. For example, in some embodiments, the arm illustrated in FIG. 1C is adjustable (e.g. by telescoping of humerus segment 112) is adjustable to the configuration illustrated in FIG. 1D.

In some embodiments, extension and/or retraction of one or more segment is effected by a portion connected to the segment (e.g. a segment extension) being moved with respect to other portions of a surgical arm. For example, in some embodiments, a segment extension is moved (e.g. by a motor located in a motor unit) to increase a length of a segment. In some embodiments, a motor uses a screw mechanism to move the segment extension.

In some embodiments, a device arm has at least the freedom of movement of human arms. Generally, segments of human limbs (e.g. arms, legs) move by flexion and extension from a proximal segment joint, and rotation around the proximal segment joint. For example, a human radius flexes and extends at the elbow and rotates around the elbow.

The term proximal joint herein refers to the joint which is least removed from the torso to which a segment is coupled, e.g. a hand proximal joint is the wrist, a radius proximal joint is the elbow joint, a humerus proximal joint is the shoulder joint.

The term proximal segment herein refers to the segment which is least removed from the torso to which a segment is coupled (e.g. by a proximal segment joint). For example, a hand proximal segment is the radius, a radius proximal segment is the humerus, and a humerus proximal segment is the torso.

In some embodiments, one or more joint is uni-directionally bendable and extendable. In some embodiments, segment rotation around a segment proximal joint is achieved by rotation of a proximal segment around a proximal segment long axis. For example, rotation of the hand around the wrist joint is by rotation of the radius around a radius long axis.

Generally, human freedom of movement for arms includes limits to the angles of rotation and flexion. Optionally, in some embodiments, the device is restricted to human freedom of movements e.g. during one or more control mode. Alternatively, the device is configured to allow movement having additional degrees of freedom relative to human arm movement.

Figure 2:
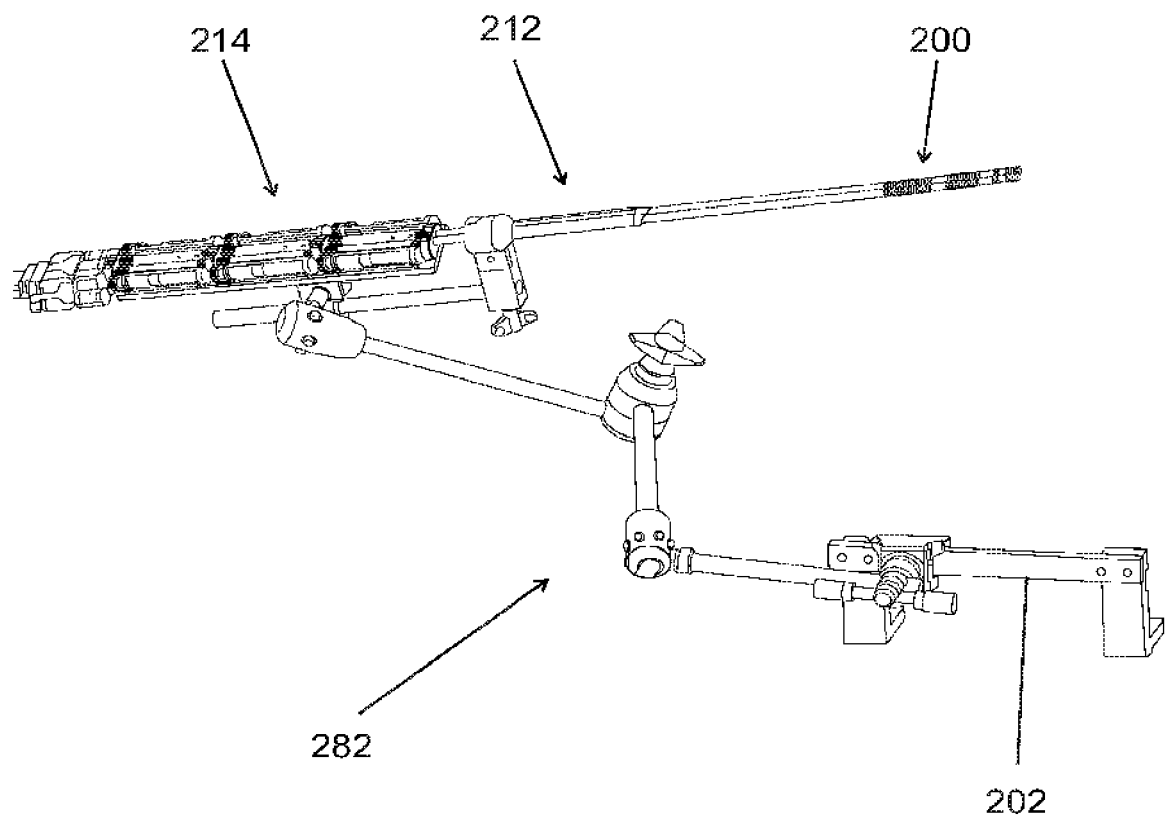
FIG. 2 is a simplified schematic of a device, held by a support, according to some embodiments of the invention.

FIG. 2 is a simplified schematic of a device 200, held by a support 282, according to some embodiments of the invention.

In some embodiments, support 282 attaches to a portion of a patient operating surface, e.g. rail 202. In some embodiments, position of attachment of support 282 on rail 202 is adjustable, for example enabling linear adjustment of position of attachment of the support to the patient operating surface. Optionally, the adjustment is performed manually.

In some embodiments, support 282 is attached to port 212 of a motor unit 214, device 200 being supported by attachment to motor unit 214.

In some embodiments, port 212 is placed at an opening to the patient's body, for example at an incision and/or at a natural body orifice such as the vagina and/or anus and/or mouth. In some embodiments, port 212 is attached to the patient's body using sutures and/or other attachment means. Additionally or alternatively, port 212 is fixated to the operating surface 202.

In some embodiments, support 282 includes a plurality of articulations where angles between segments and/or segment lengths are adjustable, for example, enabling adjustment of position and/or angle of a device 200 including surgical arms and/or a port 212 and/or motor unit 214 (e.g. which actuate device 200 arm/s).

In some embodiments, one or more motor is used to move device 200, with respect to one or more portion of the system (e.g. with respect to port 212 and/or motor unit 214), for example, into and/or out of a patient. In some embodiments, motor unit 214 includes one or more motor for movement of one or more device arm with respect to the motor unit, where, for example, one or more support segment position is changed with respect to the motor unit. In some embodiments, movement of device 200 is controlled by a user, optionally using input object control and/or a user interface.

Figure 3A:
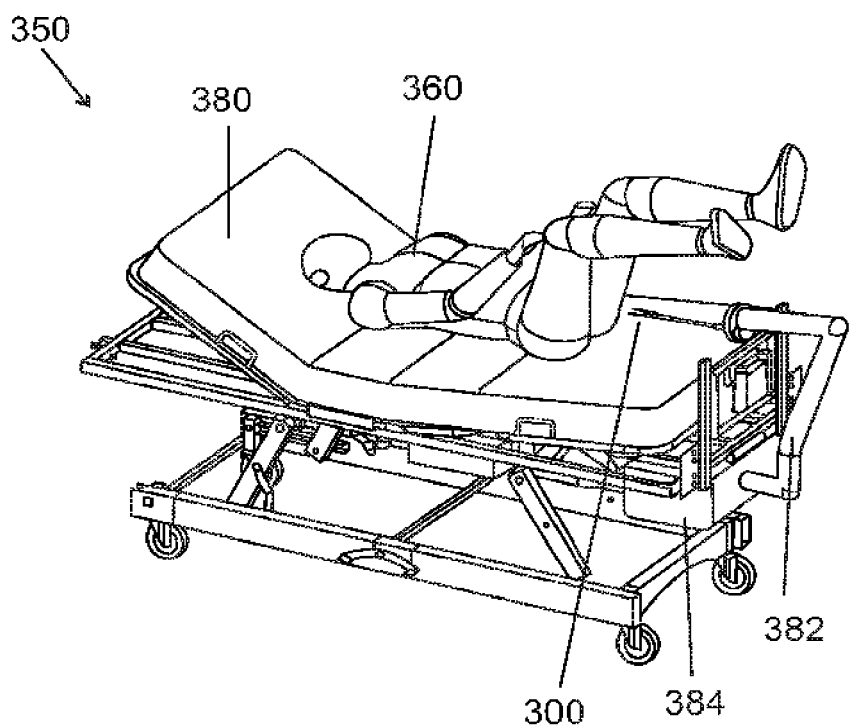
FIGS. 3A-B are simplified schematic views of a system where a device is held by a support, according to some embodiments of the invention.

FIG. 3A is a simplified schematic view of a system 350 where a device 300 is held by a support 382, according to some embodiments of the invention.

In some embodiments, a device 300 is coupled to a bed 380. In some embodiments, a patient 360 lies on bed 380 for surgical procedures using device 300. In some embodiments, one or more component of the device, for example one or more part of device control (e.g. motors) is located underneath bed, e.g. in a housing 384. In some embodiments, support 382 connects device 300 to housing 384. Optionally, other components, for example transformers, connectivity to other components e.g. the display, are located in housing 384.

In an exemplary embodiment, a main motor unit for control of movement of the device is located in housing 384, where for example, in some embodiments, torque transfer element/s transfer torque from motor/s within housing 384 to device 300 and/or elongated elements for effecting flexion of device joints are coupled to motors within housing 384.

In some embodiments, control of movement of the device above the bed, using a motor unit underneath the bed is via an orientation controller, for example using a parallelogram linkage, e.g. as described in International Patent Application Publication No. WO2011/036626 which is herein incorporated by reference into the specification in its entirety.

A potential benefit of one or more component being located underneath a bed (e.g. inside housing 384), is reduced footprint of the system in an operating room. A further potential benefit of components being located underneath a bed as opposed to above and/or around the bed is potentially improved access to a patient (e.g. in an emergency situation).

A potential benefit of the device being coupled to a bed is the ability to move and/or change an angle of the bed, for example, during surgery, while the device remains in the same position relative to the bed and/or patient. Alternatively, or additionally, in some embodiments, a device position with respect to the patient and/or the bed is adjustable, for example, before treatment with the device and/or during surgery.

Optionally, in some embodiments, support 382 moves device into position for surgery. In some embodiments, support 382 moves device into a desired position for insertion into patient 360. In some embodiments, support 382 moves device vertically, and/or horizontally, and/or laterally, and/or inserts device 300 into a patient 360 and/or withdraws device 1100 from the patient.

In the embodiment illustrated by FIG. 3A, support arm 382 and housing 384 are located at the foot end of 384. A potential benefit of this location is ease of surgery through a patient's undercarriage, for example, through the vagina. In FIG. 3A, patient 360 is illustrated in a suitable position for insertion of the device into the vagina, the patient's legs are elevated and apart (e.g. held by stirrups which are not shown).

Figure 3B:
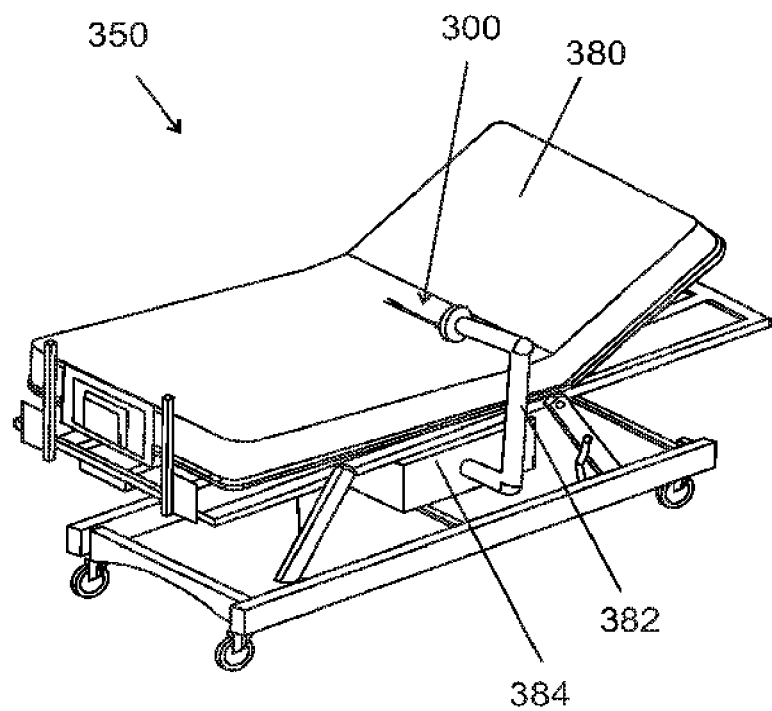

FIG. 3B is a simplified schematic view of a system 350 where a device 300 is held by a support 382, according to some embodiments of the invention. In the embodiment illustrated by FIG. 3B, support arm 382 and housing 384 are located at a long axis center of the bed 380. A potential benefit of this location is ease of abdominal and/or thoracic surgery using the device.

In some embodiments, a housing position underneath the bed and/or a position around the bed from where the arm meets the housing are adjustable. For example, the arm and/or housing are moved for different surgeries.

Figures 4A, 4B:
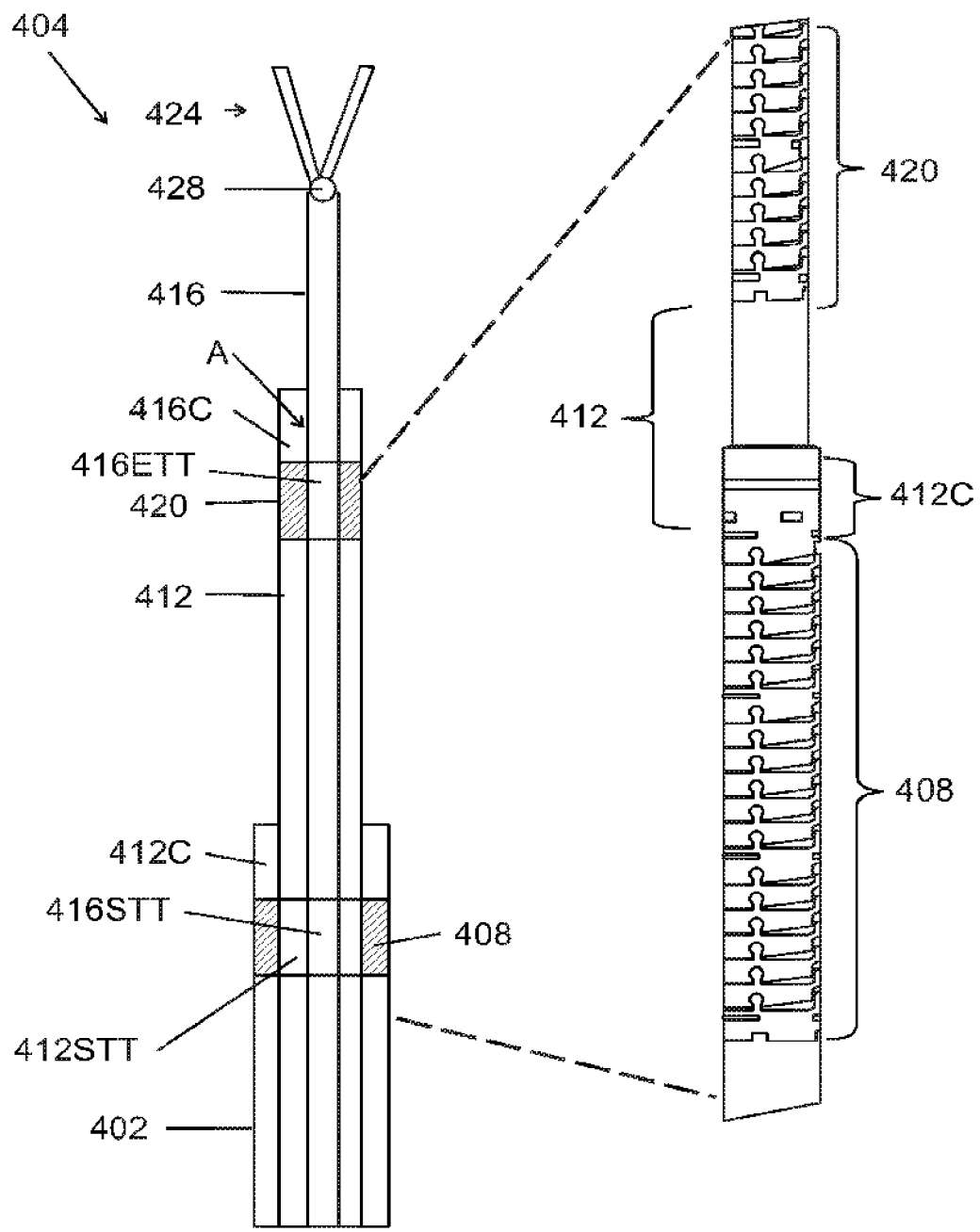
FIG. 4A is a simplified schematic cross sectional view of an arm with nested segment extensions, according to some embodiments of the invention.
FIG. 4B is a simplified schematic of a side view of a portion of an arm, according to some embodiments of the invention.

FIG. 4A is a simplified schematic cross sectional view of an arm 404 with nested segment extensions, according to some embodiments of the invention. FIG. 4B is a simplified schematic of a side view of a portion of an arm, according to some embodiments of the invention. Dashed lines illustrate the portion of the arm illustrated in FIG. 4A illustrated by FIG. 4B.

In some embodiments, arm 404 includes a hand tool 424 coupled to a radius 416 at a wrist joint 428.

In some embodiments, radius 416 is coupled to a radius extension including two torque transfer portions; an elbow torque transfer portion 416ETT disposed inside an elbow joint 420 and a shoulder torque transfer portion 416STT disposed inside a shoulder joint 408. In some embodiments, radius 416 is coupled to a humerus 412 by a connector 416C. In some embodiments, portion 416C connects radius 416 to humerus 412 whilst allowing free rotation of humerus 412. In some embodiments, at region A of FIG. 4A, protrusion/s on radius portion 416 fit into indentation/s on portion 416C. In an exemplary embodiment, a ring shaped protrusion on radius portion 416 (e.g. a ring of material connected (e.g. welded) to radius portion 416) fits into an indentation on portion 416C. Similarly, in some embodiments, portions 412C and 412 are connected by matching protrusion/s and indentation/s (e.g. a ring protrusion on portion 412 fitting into a matching indention in portion 412C).

In some embodiments, a "connecting section" includes a connector and a joint, for example shoulder joint 408 and connector 412C, and for example elbow joint 420 and connector 416C.

Figure 4C:
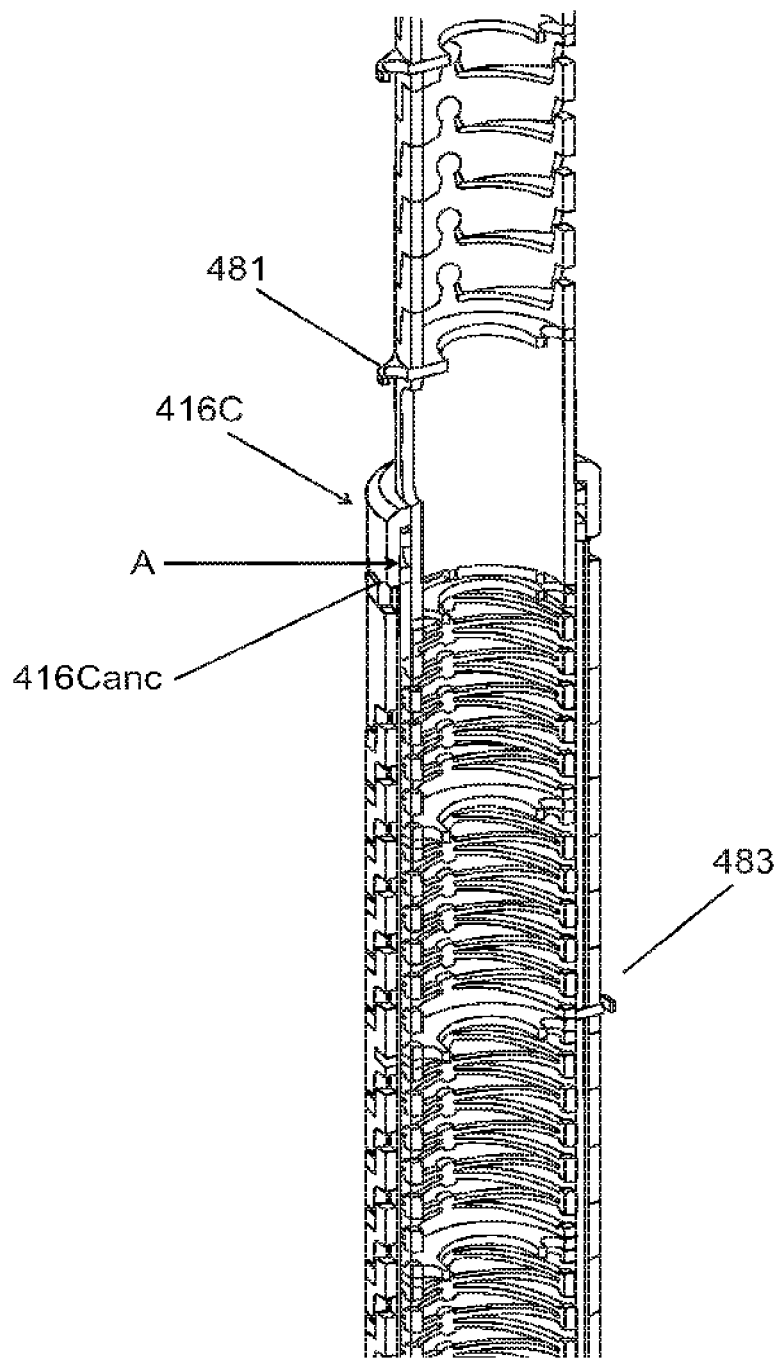
FIG. 4C is a simplified schematic cross sectional view of an arm with nested segment extensions, according to some embodiments of the invention.

FIG. 4C is a simplified schematic cross sectional view of a portion of an arm, according to some embodiments of the invention. In some embodiments, for example, a portion includes a ring protrusion which fits into an indentation on portion 416C.

In some embodiments, portion 416C provides anchoring to one or more elongated element: for example, where elongated element/s (e.g. a cable, a wire, a tape) are connected/coupled to portion 416Canc.

In some embodiments, one or more connector couples portions whilst allowing one portion to rotate within the connector about the portion's long axis. For example connecting portion 416C allows radius 416 to rotate within connecting portion 416C about a radius long axis.

In some embodiments, humerus 412 is coupled to a humerus extension including one torque transfer portion, a shoulder torque transfer portion 412STT disposed inside shoulder joint 408. In some embodiments, the humerus is coupled to a torso 402 by a connector 412C.

In some embodiments, a surgical arm includes a first and a section flexible portion (e.g. elbow joint and shoulder joint) which are coupled together with a short connecting segment (e.g. a humerus section coupling a shoulder and elbow joint is short). In some embodiments, coupling between the flexible portions is a point connection (e.g. a shoulder and elbow joint are directly connected).

In some embodiments, a rigid anchoring portion (e.g. portion 416C) connects two flexible portions, where the anchoring portion provides anchoring of elongated elements which control flexion and extension of the joint which is, for example, proximal to the elongated portion. In some embodiments, anchoring is provided by a portion of one of the joints, e.g. a distal portion of the proximal joint.

In some embodiments, one or more shafts (or portions thereof) of the surgical arm are rigid. In some embodiments, a flexible shaft is nested within a rigid outer shaft. In some embodiments, the outer shaft is flexible to a lower extent than the inner shaft.

Figure 5:
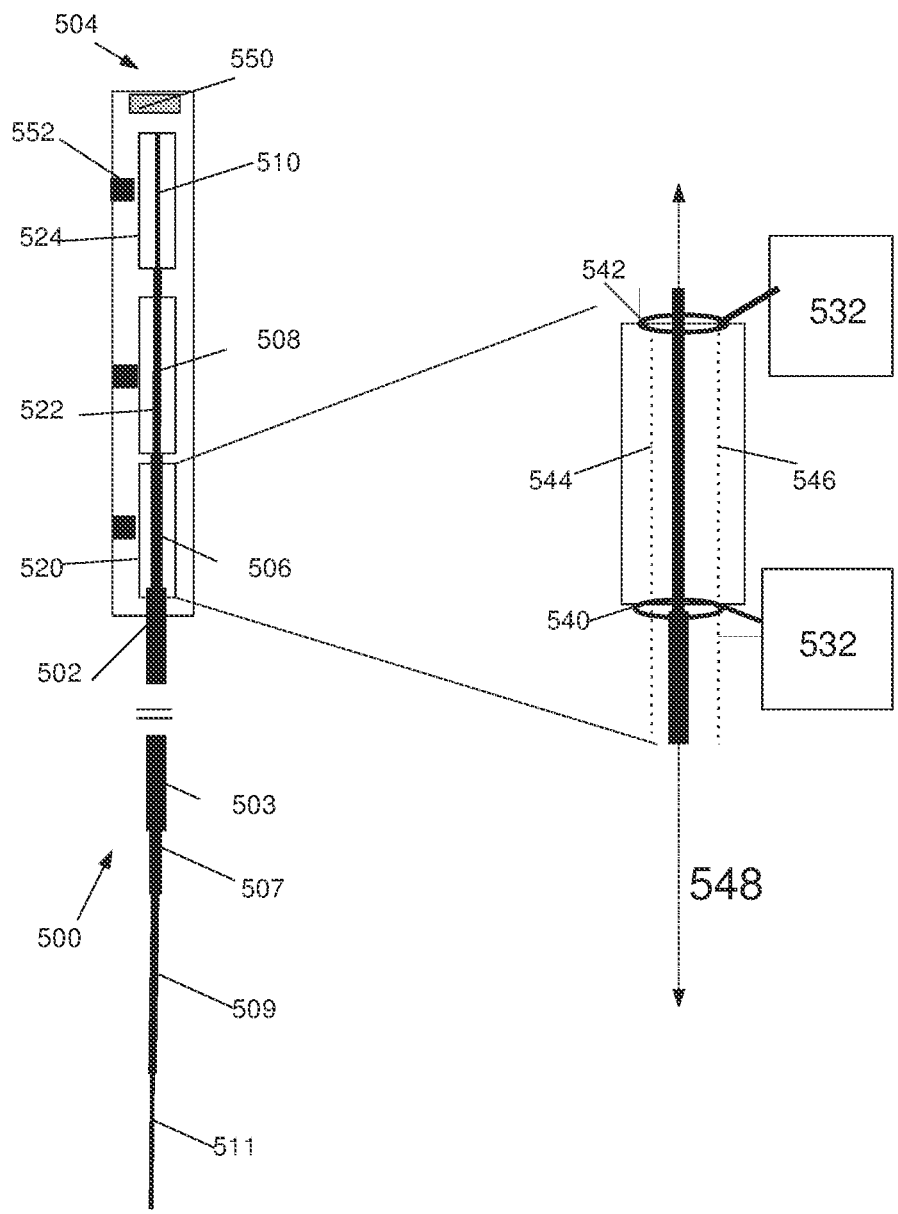
FIG. 5 is a schematic diagram of actuation of a surgical arm, according to some embodiments of the invention.

FIG. 5 schematically illustrates actuation of a surgical arm 500, according to some embodiments.

In some embodiments, a proximally extending shaft extension 502 (e.g. an extension of a torso 503) of arm 500 is attached to a motor unit 504. In some embodiments, proximal shaft extensions of arm segments that are nested within extension 502 (e.g. a proximal shaft extension 506 of humerus 507, a proximal shaft extension 508 of radius 509 that is nested within humerus extension 506, a proximal shaft extension 510 of a hand portion 511 that is nested within radius extension 508, and so forth) are actuated by a plurality of actuation mechanisms of the motor unit, such as 3 actuation mechanisms 520, 522 and 524. In some embodiments, the number of actuation mechanisms is set in accordance with the number of joints of the arm, for example, as shown herein, an arm including 3 joints (e.g. shoulder, elbow and wrist joints) is actuated by 3 actuation mechanisms, an arm including 4 joints is actuated by 4 actuation mechanisms, an arm including 2 joints is actuated by 2 actuation mechanisms, an arm including 1 joint is actuated by a single actuation mechanism.

In some embodiments, an actuation mechanism 520 (shown in the enlarged view) is configured to move at least a segment of arm 500, for example rotate the segment and/or bend the segment and/or otherwise move the segment. In some embodiments, an actuation mechanism comprises one or more actuators, for example 1, 2, 3, 4, 5 and/or 6 actuators. In some embodiments, the actuators are independently operable, yet, in some embodiments, a shaft manipulation (e.g. rotation, bending) obtained by a first actuator effects control of one or more other actuators.

In some embodiments, actuators of the same actuation mechanism are actuated together. Additionally or alternatively, actuators of different actuation mechanisms are actuated together, for example to provide for articulation of a proximal arm segment, a distal arm segment (which is at least partially nested within the proximal arm segment) needs to be moved as well. In an example, to provide for flexion of the shoulder, a bending actuator of an elbow is actuated as well.

In some embodiments, for example as shown herein, shaft extensions 502 and 506 (which is nested, in part, within shaft extension 502) are received within actuation mechanism 520. In some embodiments, actuation mechanism 520 comprises a first actuator 540, and a second actuator 542. In some embodiments, first actuator 540 is configured to rotate an arm portion, such as rotate the torso by rotating shaft extension 502 around its axis. In some embodiments, second actuator 542 is configured to bend an arm portion, such as bend a shoulder joint at a distal end of the torso (not shown herein). Optionally, bending is achieved by respective linear movement of elongate elements 544 and 546, which extend from actuator 542 and are connected distally to the joint.

In some embodiments, a prime mover of an actuator such as 540 and/or 542 comprises a motor 532. In some embodiments, a speed of motor 532 ranges between, for example, 10-100 rpm, such as 20 rpm, 50 rpm, 70 rpm, 80 rpm or intermediate, higher or lower speeds. In some embodiments, motor 532 is configured to apply a torque between 0.5 N*M to 3 N*m, such as 1 N*m, 1.5 N*m, 2 N*m or intermediate, higher or lower values. In some embodiments, motor 532 is a continuous rotation motor.

Additionally or alternatively, a prime mover of an actuator comprises a linear motor. Additionally or alternatively, a prime mover of an actuator comprises a pulley. In some embodiments, the prime mover of an actuator is manually operated, for example comprising one or more cables that are pulled on to actuate movement of the gear.

In some embodiments, a single motor is configured to move more than one actuator (e.g. rotate both the bending and rotation gears). In some embodiments, dual-actuation is enabled by use of a locking mechanism and another motor configured for switching between the actuators, based on the selected articulation (e.g. bending or rotation).

In some embodiments, motor 532 is positioned parallel to the shaft extension, for example underlying the shaft extension, overlying the extension and/or positioned beside the extension. Alternatively, motor 532 is disposed within an internal lumen of the shaft extension. Alternatively, the shaft extension is configured as a part of the motor, for example contained within an external housing of motor 532.

In some embodiments, an actuator comprises a single gear or a gear train. In some embodiments, the gear train is configured to amplify the input torque generated by motor 532. Alternatively, the gear train is configured to reduce the input torque generated by motor 532. In some embodiments, the gear train is configured to reduce the rotation speed generated by the motor. In an example, the motor speed is 12,000 RPM, and the gear or gear train reduce the speed by a ratio of, for example, 134:1, 43:1, 9:1 and/or intermediate, higher or lower ratios. In an example, a gear or gear train actuating movement of an end-effecter of the arm such as grippers is configured to reduce the speed by a ratio of 9:1, enabling fast opening and closure of the gripper. This may be advantageous, for example, when dissecting tissue using the gripper.

Alternatively, in some embodiments, the gear train is configured to increase the output speed generated by the motor. In an example, the output speed of the motor is increased for autonomous electrical ablation of tissue.

In some embodiments, actuators of an actuation mechanism comprise gears or gear trains that are different from each other. In some embodiments, the motors of the two actuators are rotated at similar speeds, but the "final" movement manipulating gears of each actuator are rotated at different speeds. In an example, actuator 542 comprises a gear transmission while actuator 540 is driven directly by the motor. In another example, the actuators each comprise a single gear, but the gears are of different sizes and/or shapes (e.g. comprising different number of teeth).

In an example, actuator 540 comprises a gear that is configured to rotate shaft extension 502 directly, rotating at a speed, of, for example, 2000 RPM; actuator 542 comprises a gear that is configured to actuate bending by linearly moving elongated elements 544 and 546, optionally by rotation of a threaded screw coupled to the elements for example as described hereinbelow, and due to this additional transmission the gear of actuator 542 needs to rotated faster than gear 540, for example rotated at a speed of 4000 RPM.

In another example, an actuator that actuates an end-effecter such as a gripper is configured to rotate at a relatively fast speed, for example 9000 RPM for enabling fast movement.

Alternatively, in some embodiments, it is desired to actuate an end-effecter at a relatively low speed, for example for action requiring applying of relatively large force via the end-effecter, such as separating tissue, stapling tissue, and/or other actions.

In some embodiments, actuators 540 and 542 are rotated on a single rotational axis 548. In some embodiments, axis 548 is also the rotational axis of shaft extensions 502 and 506.

In some embodiments, actuation mechanisms 520, 522, 524 of the motor unit are collinear.

In some embodiments, the motor unit includes one or more position sensor 552.

In some embodiments, position sensor 552 is placed adjacent the motor for sensing a current rotation angle of the motor.

In some embodiments, the position sensor is magnetically operated, using a magnet placed on the motor gear and sensing the magnetic flux to determine a current position of the motor gear.

In some embodiments, the motor unit is controlled by a processor 550 including a memory which stores commands.

In some embodiments, data from position sensor/s and/or from control memory is used to infer a position of device portion/s.

In some embodiments, the motor unit is controlled by a processor configured in the user's input device.

Figure 16:
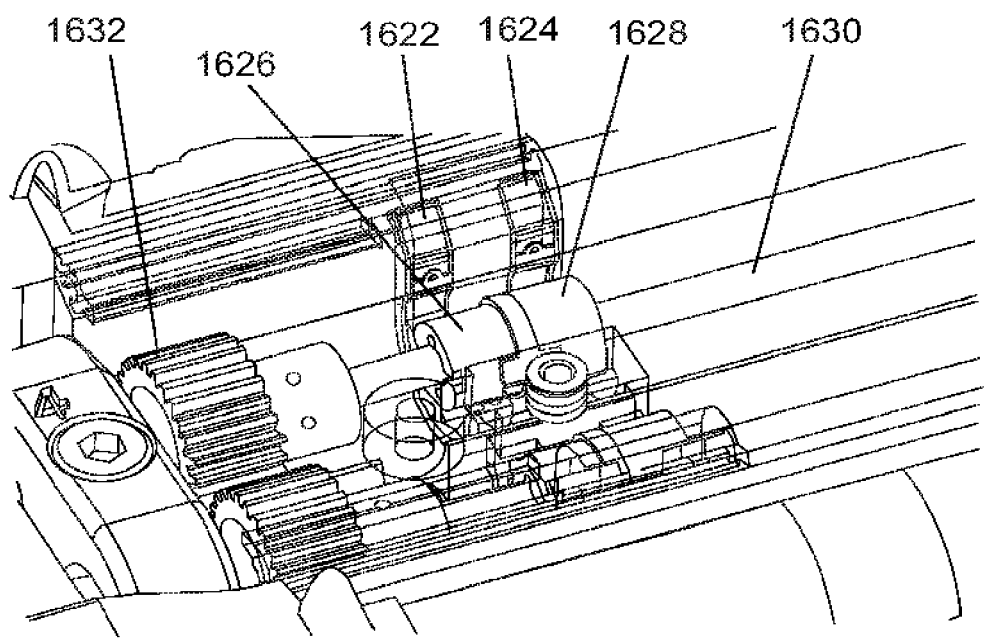
FIG. 16 is a simplified side view of a portion of a motor unit including elements for supplying electric power to an end effecter of the surgical arm, according to some embodiments of the invention.

In some embodiments, motor unit 504 includes structure (e.g. including electrical contact/s), for example, for delivery of monopolar and/or bipolar energy to the device (e.g. to a device end effecter), for example as further described in FIG. 16.

Figure 6A:
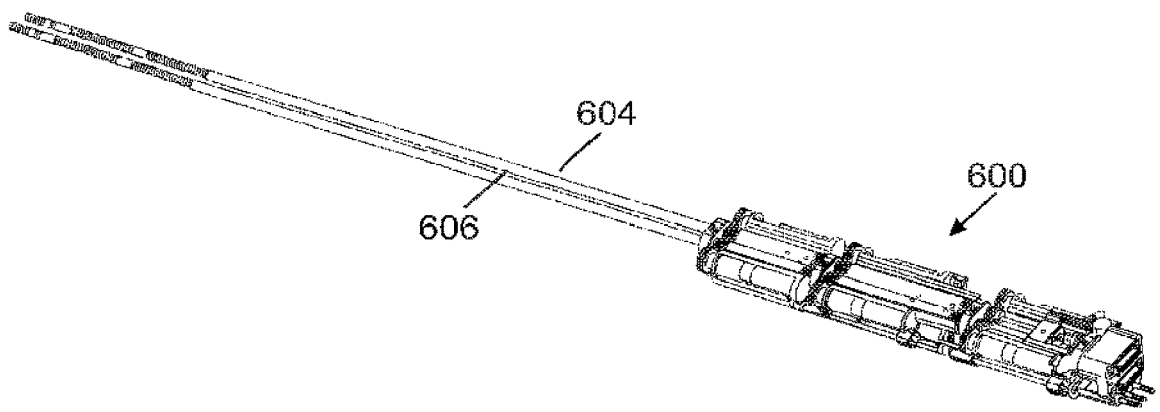
FIGS. 6A-D are various views of a motor unit for actuating a surgical arm, according to some embodiments of the invention.

FIG. 6A is a simplified schematic side view of a motor unit 600 for actuation of a device including surgical arms, according to some embodiments of the invention. In some embodiments, a device including a first surgical arm 604 and a second surgical arm 606 are controlled by motor unit 600.

Figure 6B:
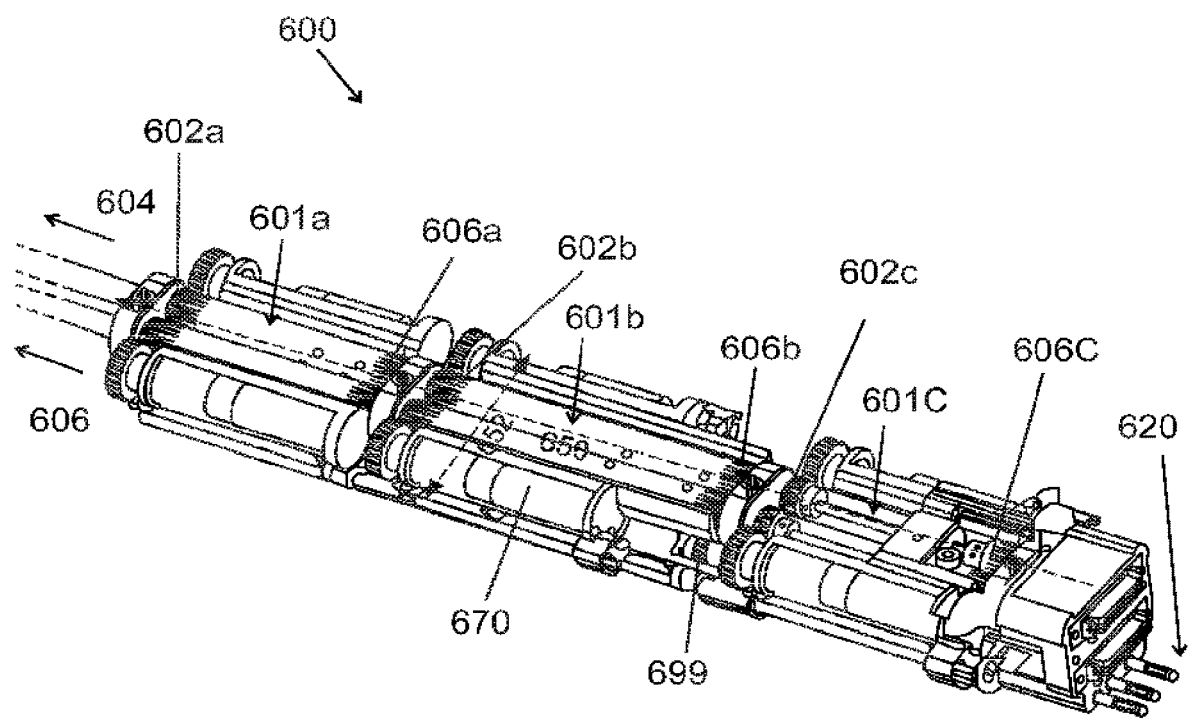

FIG. 6B is a detailed view of the motor unit 600, according to some embodiments.

In some embodiments, a first actuation mechanism 601*a*, including first rotation gear 602*a* and first bending gear 606*a*, drives flexion/extension and rotation of a shoulder joint. Referring now to FIGS. 4A-B, for example, in some embodiments, first actuation mechanism 601*a* rotates the shoulder joint by rotating torso 402 and effects flexion and extension of shoulder joint 408 by movement of elongated elements attached to connector 412C.

In some embodiments, a second actuation mechanism 601*b*, including second rotation gear 602*b* and second bending gear 606*b*, drives flexion/extension and rotation of an elbow joint.

In some embodiments, one or more driving gear coupled to a motor 670 is disposed underneath motor unit 600. For example, in some embodiments, a gear which drives second bending gear 606*b*, which gear is coupled to a motor is disposed on an underside of motor unit 600. For example, gear 699 drives a second actuation mechanism corresponding to second surgical arm 606. Referring now to FIGS. 4A-B, for example, in some embodiments, second actuation mechanism 601*b* rotates the elbow joint by rotating humerus 412 and effects flexion and extension of elbow joint 420 by movement of elongated elements attached to portion 416C.

In some embodiments, a third actuation mechanism 601*c*, including third rotation gear 602*c* and third bending gear 606*c*, actuates an end effecter (e.g. opens and closes a gripper) and drives rotation of a wrist joint. Referring to FIG. 4A, in some embodiments, rotation gear 602*c* rotates radius 416 and bending gear 606*c* actuates hand tool 424; For example, in some embodiments, rotation of third bending gear 606*c* opens and closes an end effecter.

In some embodiments, similarly, second surgical arm 606 is actuated by three actuation mechanisms, including, for example, 6 motors. In an exemplary embodiment, a device for insertion into the body includes two surgical arms, actuated by 12 motors.

In some embodiments, one or more additional motor (e.g. a 13th motor) moves the device arms towards and/or away from the motor unit. For example, in some embodiments, a position of attachment of the motor unit (e.g. to a support and/or to a patient support surface) is changed e.g. by a motor.

In some embodiments, the device comprises a single arm actuated by a motor unit comprising 6 motors (e.g. 2 motors per each actuation mechanism). In some embodiments, a $7^{th}$ motor is used for linearly moving the arm, for example towards and/or away from the motor unit and/or from the patient's body.

In some embodiments, one or more additional motors (e.g. an $8^{th}$ motor, a $9^{th}$ motor) are used. Optionally, the additional motor(s) actuate movement of an end-effecter of the arm around a pivot point (fulcrum movement), for example around the incision.

For example, referring to FIG. 2, in some embodiments, a position of attachment of support 282 with respect to rail 202 is changed (e.g. by a motor located on support 282). For example, in some embodiments, a position of attachment of motor unit 214 with respect to support 1482 is changed (e.g. by a motor located on support 282).

For example, moving the device into and/or out of a patient body e.g. when the motor unit is supported in a fixed configuration and/or to automate movement of the device into the patient. In some embodiments, a motor located within motor unit 600 moves the device arms into and/or out of a patient.

In some embodiments, for example, so that rotation of a joint also causes rotation of joints distal of the rotated joint, more than one actuation mechanism is driven in rotation of the joint. For example, in some embodiments, for rotation of the shoulder joint, gears 602*a*, 606*a*, 602*b*, 606*b*, 602*c*, 606*c* are rotated in the same direction. For example, in some embodiments, for rotation of the elbow joint, gears 602*b*, 606*b*, 602*c*, 606*c* are rotated in the same direction. For example, in some embodiments, for rotation of the end effecter, gears 602*c*, 606*c* are rotated in the same direction.

In some embodiments, concurrent rotation of nested portions with outer portions prevents stress on and/or tangling of internal elongated elements (e.g. elongated element/s which are used to effect flexion/extension, e.g. elongated element/s providing power supply).

In some embodiments, one or more actuation mechanism is used to flex/extend a joint. For example, in some embodiments, to bend a shoulder joint, elongated elements for bending of both the shoulder joint and elbow joint are moved, for example by actuating bending gear 606*a* and bending gear 606*b*.

In some embodiments, if elongated elements for the elbow are not moved and/or released, tension in the elongated elements associated with the elbow joint resist movement of the shoulder joint.

In some embodiments, a motor unit is small, for example having a long axis length 650 of between 100-600 mm, or 200-400 mm, or 300-500 mm, or 150-400 mm, or intermediate, longer or shorter length. In some embodiments, a width 652 of the motor unit (e.g. as measured perpendicular to the long axis) is between 20-100 mm, or 30-80 mm, or 50-70 mm, or intermediate, longer or shorter width.

In some embodiments, motor 670 is cylindrical. Optionally, a diameter of motor 670 is less than 17 mm, less than 35 mm, less than 10 mm or intermediate, larger or smaller diameters. A potential advantage of disposing a motor of a relatively small diameter in a parallel position relative to the arm may include maintaining the dimensions of the motor unit small.

Alternatively, the motor is not cylindrical, for example rectangular. In some embodiments, the motor comprises a hollow shaft. A potential advantage of a hollow shaft may include reducing the footprint of the system in the operating room.

In some embodiments, electric power is supplied through wires to the motor unit, for example, in some embodiments, contacts 620 are connected to an electric power supply. The electric power supply may include a battery (optionally rechargeable) and/or a generator and/or connection to the electrical network via a wall socket and/or a combination thereof. In some embodiments, the power range is between 100-300 W, for example 150 W, 200 W, 250 W or intermediate, higher or lower ranges. In some embodiments, an uninterruptible power supply source is used to protect from power interruptions.

In some embodiments, a motor unit drives more than two surgical arms and/or drives additional device elements. For example, in some embodiments, a motor unit drives two device arms and a camera.

Figure 6C:
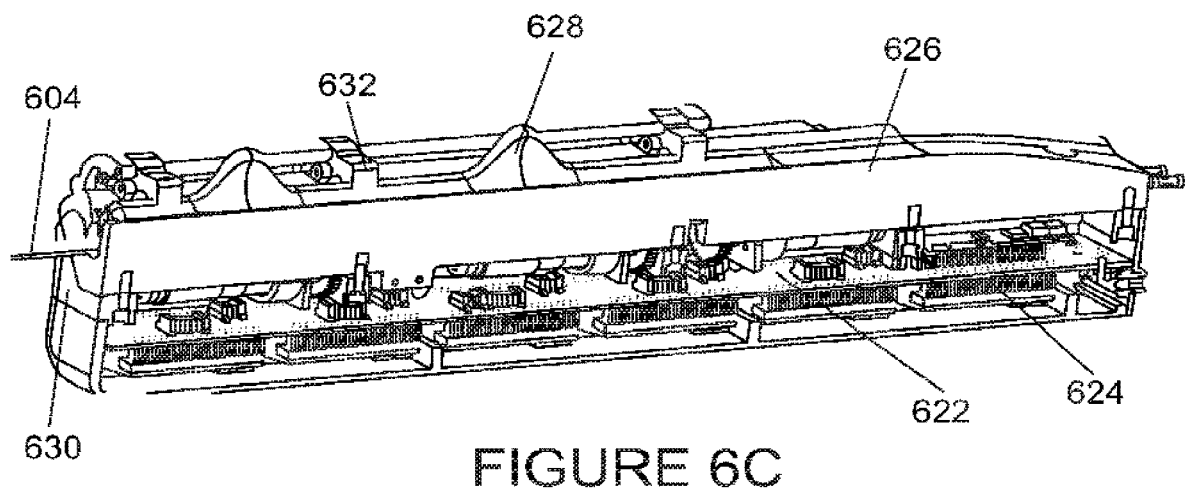

FIG. 6C is a cross-section of the motor unit along the length of the unit, showing actuation mechanisms of a single surgical arm, according to some embodiments. In some embodiments, the motor unit comprises a motherboard 622, optionally underlying the actuation mechanisms. In some embodiments, one or more driver circuits 624 are operably coupled to motherboard 622 for controlling operation of the motor unit. In some embodiments, each driver circuit is configured to control activation of one of the motors (e.g. one of the 6 motors described hereinabove). In some embodiments, cross-control of the motors is provided. In an example, a position sensor of a first motor is controlled by a controller of a second motor. Optionally, in such configuration, malfunctioning of the first motor, position sensor associated with the first motor and/or driver controlling the first motor can be detected by the controller of the second motor.

In some embodiments, an external housing 626 of the motor unit comprises a handle 628 for attaching and/or releasing arm 604 from a distal end face 630 of the motor unit.

In some embodiments, one or more latches 632 are configured on external housing. Optionally, latch 632 is configured to release a gear fixation mechanism used, for example, during attachment of the surgical arm to the motor unit to maintain calibration of the motor unit, for example as further described herein.

Figure 6D:
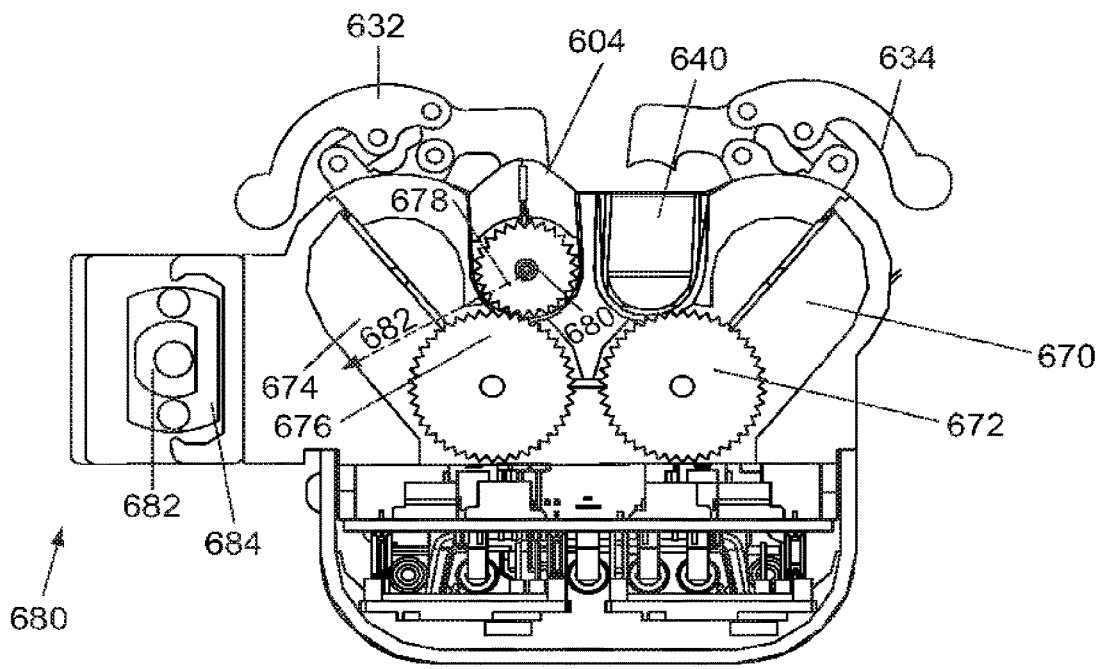

FIG. 6D is a cross section of the motor unit along an axis perpendicular to the long axis, according to some embodiments.

In some embodiments, the motor unit is configured to actuate two surgical arms; in this example, one surgical arm 604 (an extension of which) is shown to be received within a first side of the motor unit, while the second opposing side is shown in a configuration suitable for receiving a second arm, for example within internal lumen 640.

It is noted that in some embodiments a motor unit configured for actuating a single arm is comprised of only of one of the sides of the motor unit shown herein, including, for example, 3 actuation mechanisms.

In some embodiments, for example as shown herein, actuation gears 672 and 676 of motors 670 and 674 respectively are each configured to drive a gear of an actuation mechanism, for example actuation gear 672 of motor 670 is configured to drive rotation gear or bending gear 678 (such as gear 602a or 606a or 602b or 606b or 602c or 606c).

In some embodiments, latch 632 configured at the first side of the motor unit in which the arm is received is shown at a closed position, which releases a fixation mechanism of gear 678, allowing it to rotate freely; a second latch 634 configured at the second side of the motor unit, shown without an arm, is shown at an open, lifted position.

In some embodiments, a motor such as 674 is disposed such that it does not extend to a distance 682 longer than 5 mm, 10 mm, 20 mm or intermediate, longer or shorter distances relative to a central long axis of an actuation mechanism, for example passing through a center 680 of rotation/bending gear. A potential advantage of a motor disposed adjacent an actuation mechanism, optionally in parallel to the actuation mechanism such that it substantially does not protrude outwardly or protrudes outwardly to a short distance only may include reducing bulkiness of the motor unit, potentially allowing insertion of the surgical arm(s) as well as the motor unit into the body during operation.

In some embodiments, the motor unit is coupled to a linear unit 680, configured for actuating linear movement of the motor unit (and thereby of the arm(s)), for example actuate advancement and/or retraction of the device to and/or from the patient body. In some embodiments, linear unit 680 comprises a rail 682 on which a sliding element 684 coupled to the motor unit can be moved linearly. In some embodiments, movement (e.g. sliding) of the motor unit on the rail of the linear unit is actuated by a motor.

Alternatively, in some embodiments, the linear unit is an integral component of the motor unit.

In some embodiments, the linear unit comprises one or more sensors, such as microswitches, for detecting movement of the motor unit. In some embodiments, the linear unit comprises one or more actuation buttons configured to provide for a user (e.g. nurse) to move the motor unit according to the need. In some embodiments, the motor driving the linear movement (not shown herein) comprises an electro-magnetic break. Optionally, the brake is configured to avoid unwanted movement (e.g. slipping) of the motor unit, for example during a power outage.

Figure 7:
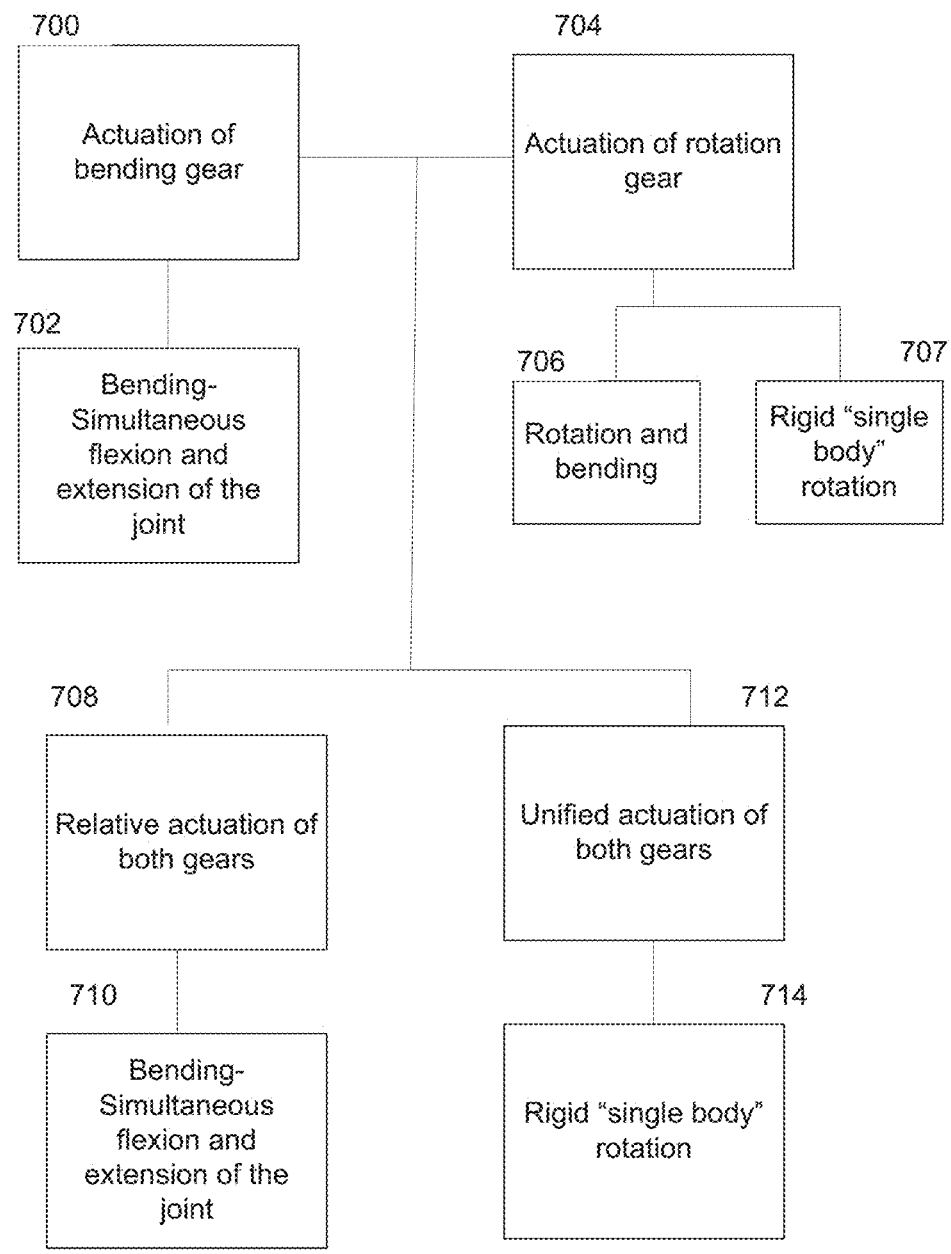
FIG. 7 is a flowchart of gear actuation for articulating a surgical arm, according to some embodiments of the invention.

FIG. 7 is a flowchart of exemplary operation of an actuation mechanism comprising a rotation gear and a bending gear, according to some embodiments.

In some embodiments, actuation of a gear comprises actively rotating the gear at a certain speed and/or direction, for example by the motor. In some embodiments, actuation of the bending gear (700) generates bending of the joint (702), for example by simultaneous flexion and extension. Optionally, simultaneous flexion and extension is obtained by relative tensioning and releasing of elongated elements extending along the arm segment being moved and connected at a point distal to the joint (e.g. flexible segment).

In some embodiments, an articulation actuated by rotation gear (704) depends on movement of the bending gear. In some embodiments, for example when the arm is placed in the motor unit, free rotation of the bending gear is resisted at least in part by a gear that drives the bending gear, for example in some embodiments the motor gear or a second gear driven by the motor gear. Optionally, in such situation, actuation of the rotation gear whilst the bending gear is held stationary generates rotation of an arm segment proximal to the joint as well as bending of the joint (706).

In some embodiments, when no resistance is imposed on the bending gear, actuation of the rotation gear will bring about rotation of the bending gear, resulting in rigid "single body" rotation of the arm (707).

In some embodiments, both gears are actuated together.

In some embodiments, relative actuation of the gears (708), including, for example: holding the bending gear stationary and rotating the rotation gear; rotating the gears at different speeds and/or directions generates bending (710).

In some embodiments, unified actuation of both gears (712), i.e. rotating the bending gear and the rotation gear at the same speed and direction generates "single body" rotation (714), in which the actuated arm segment moves as a whole.

In some embodiments, a bending gear and/or rotation gear of more than one actuation mechanism (e.g. 2, 3, 5) are actuated simultaneously. Optionally, actuation of more distal, nested arm portion(s) is performed so as to allow movement of a more proximal arm portion. For example, when bending the shoulder joint, bending gears of both the shoulder and the elbow are actuated (e.g. 606a, 606b) so as to release tension from the elongate element operating the elbow which will in turn allow for bending of the shoulder. In an example, if 606a was to be solely rotated to bend the shoulder, a tensioned elongate element operating the elbow may tear.

Figure 8A:
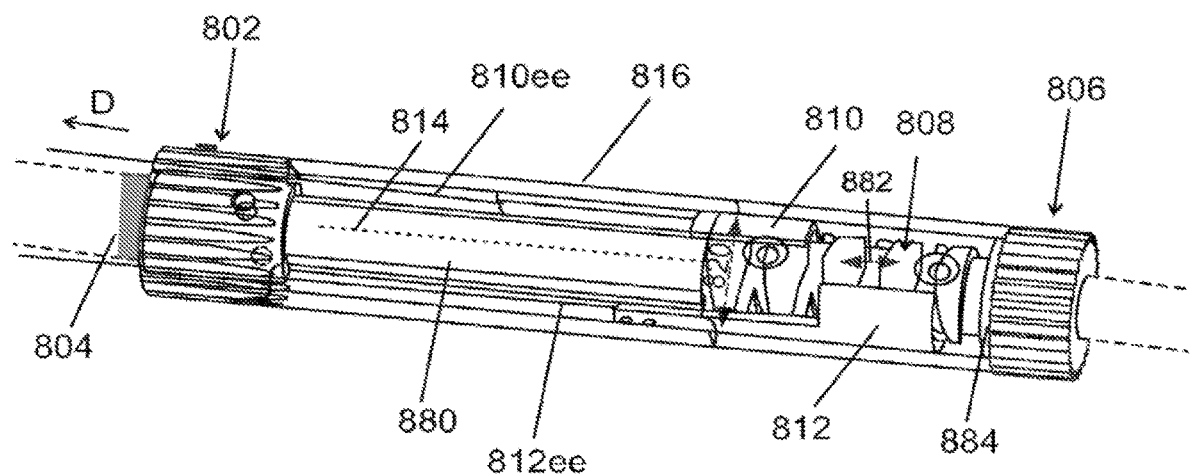
FIGS. 8A-C are various view of an actuation mechanism, according to some embodiments of the invention.

FIG. 8A is a simplified schematic side view of an actuation mechanism for control of a surgical arm joint, according to some embodiments of the invention.

In some embodiments, a rotation gear 802 is coupled to a shaft 804, where shaft 804 is coupled to an extension (e.g. to torso 402, FIG. 4A). In some embodiments, rotation of rotation gear 802 causes rotation of shaft 804 which in turn rotates the distal extension coupled to the shaft.

In some embodiments, a shaft 880 which is nested, at least in part, within shaft 804 extends in the proximal direction to a bending gear 806.

In some embodiments, bending gear 806 is coupled to a portion including screw threading, referred to herein as threaded screw 808. In some embodiments, a threading on screw 808 comprises a double thread. In some embodiments, rotation of the double thread in one direction achieves bidirectional lateral movement of one or more rider elements, such as half-nuts referred to hereinbelow, coupled to the screw.

In some embodiments, a pitch 882 of the screw thread is selected according to the use of the arm. For example, a small thread pitch is more advantageous when the arm is configured to operate large loads, for example a load of 2000 grams, 1500 grams, 3000 grams or intermediate, larger or smaller loads at a low speed (e.g. 0.5 rounds per second, 1 round per second, 0.2 rounds per second). Alternatively, a large thread pitch is more advantageous when the arm is configured to operate small loads, for example 100 grams, 50 grams, 300 grams or intermediate, larger or smaller loads at a higher speed (e.g. 2.5 rounds per second, 4 rounds per second, 5 rounds per second).

In some embodiments, rotation of the bending gear 806 causes rotation of threaded screw 808. In some embodiments, a first half nut 810 and a second half nut 812 are coupled to screw threaded screw 808 such that rotation of the screw threading generates linear movement of half-nuts parallel to a long axis 814 of central shaft 804, where first half-nut 810 and second half-nut 812 move in different directions.

In some embodiments, each of the half-nuts is limited to movement in a single direction, for example a right handed half-nut and a left handed half-nut. In some embodiments, movement of the half-nuts is limited by one or more protrusions, for example protrusions extending radially inward from an inner wall of housing 816, for example as further described herein.

In some embodiments, first half nut 810 and second half nut 812 are connected to elongated elements 810ee and 812ee respectively, where linear movement of the nuts pulls one elongated element whilst releasing and/or pushing on the other, generating flexion/extension of the joint. In some embodiments, a distance 820 between the half-nuts, measured along an axis perpendicular to the long axis, defines the distance between the elongated elements. In some embodiments, distance 820 between the elongated elements remains constant. In some embodiments, first nut 810 is configured remain in line with elongated element 810ee, and second nut 812 is configured to remain in line with elongated element 812ee.

In some embodiments, an elongated element such as 810ee and/or 812ee comprises a wire, cable, ribbon, tape and/or any other element which can be tensioned and released to provide for bending of the joint.

It is noted that in some embodiments, only one elongated element is used. In an example, the mechanism comprises one elongated element and an elastic element such as a spring. Optionally, the spring is configured to move relatively to the elongated element, for example if the elongated element is flexed, the spring is extended and vice versa. It is also noted that in some embodiments, more than two elongated elements (e.g. 3, 4, 6, 8) may be used.

In some embodiments, actuation of the rotation gear rotates the arm segment and thereby pulls on the elongated elements, moving the half-nuts. If the bending gear is held stationary (e.g. by the motor gear), the threaded screw will not rotate, generating simultaneous rotation and bending of the arm segment. If the bending gear is free to rotate, pulling on the elongated elements will in turn move the half-nuts, rotating the threaded screw. Friction at interface 884 between a head of the threaded screw and bending gear 806 will in turn rotate the bending gear, generating rotation of the arm segment as one piece.

In some embodiments, one or both of the elongated elements is coupled to an elastic element such as a spring. Optionally, the spring is configured to limit tensioning of the elongated element(s), yielding in response to a force (e.g. torque and/or pulling force) above a certain threshold.

Figure 8B:
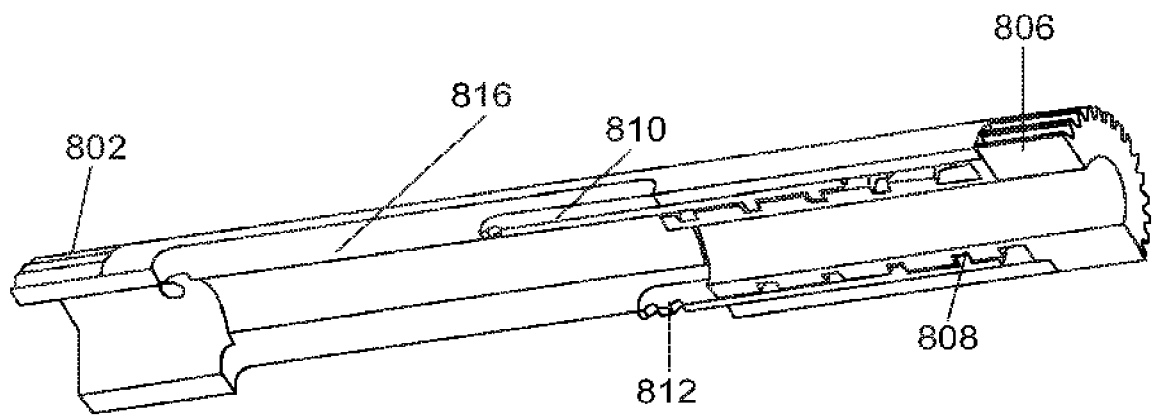
Figure 8C:
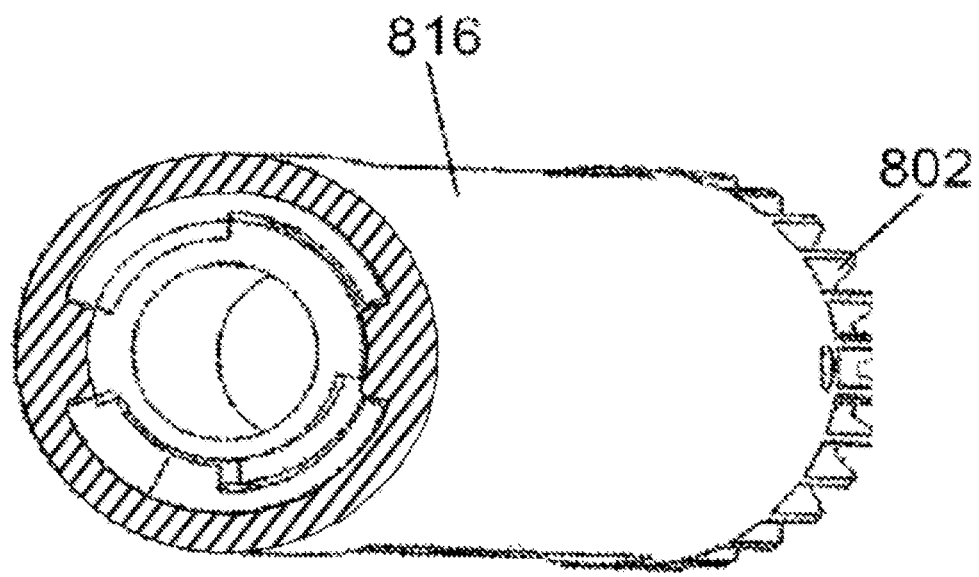

FIGS. 8B-C are cross section views of the actuation mechanism along the long axis (8B) and along an axis perpendicular to the long axis (8C). FIG. 8B show housing 816 extending between rotation gear 802 and bending gear 806. Threaded screw 808 and half-nuts 810 and 812 are shown at a cross section. FIG. 8C, viewed from a proximal to distal direction, shows radially inward protrusions 82d which are configured to limit rotational movement of the nuts, for example so as to keep a constant cross-distance between the half-nuts, for example during rotation of threaded screw 808.

In some embodiments, elongated elements 810ee and/or 812ee are positioned within designated elongated grooves 850 configured in housing 816 (see FIG. 8C) such that actuation of rotation gear 802 does not twist the elongated elements about the long axis of the actuation mechanism. Optionally, a cross-wise position of the elongated elements relative to each other is maintained constant.

In some embodiments, housing 816 covers the central shaft, screw threading and nuts, for example, potentially preventing debris or other material from entering the mechanism. In some embodiments, housing 816 is cylindrical.

In some embodiments, each mechanical device joint is coupled to an actuation mechanism as described above (e.g. by an extension coupled to the joint). For example, in some embodiments, each extension portion (e.g. as describe above) is coupled to a central shaft, and elongated portions for control of flexion and extension (e.g. as described above) are coupled to half-nuts of the actuation mechanism.

In some embodiments, actuation mechanisms for a single surgical arm are arranged linearly, with central shafts disposed in a nested configuration, the inner central shafts protruding for control by the gears.

Figure 9A:
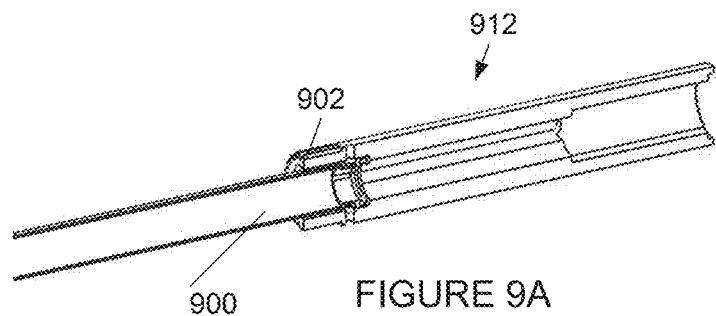
FIGS. 9A-D schematically illustrate, at a cross section, different layers of a structure of the actuation mechanism for articulating nested arm segments, according to some embodiments of the invention.
Figure 9B:
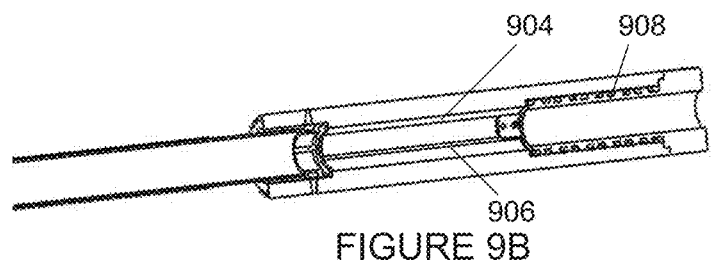
Figure 9C:
Figure 9D:
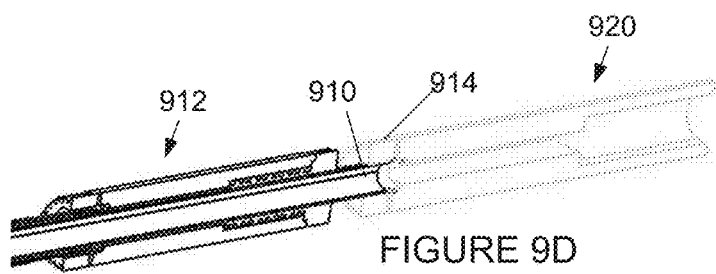

FIGS. 9A-D schematically illustrates, at a cross section, different layers of a structure of the actuation mechanism for articulating nested arm segments, according to some embodiments. In FIG. 9A, an extension 900 of the shoulder (e.g. a torso for example as shown in FIG. 4A) is operably received within a rotation gear 902 of a first actuation mechanism 912, according to some embodiments. FIG. 9B illustrates elongated elements 904 and 906 for actuating bending of the shoulder in response to rotation of threaded screw 908, according to some embodiments. In FIG. 9C, an extension 910 of the elbow (e.g. an extension of a humerus 412 for example as shown in FIG. 4A), which is nested, at least in part, inside extension 900 of the shoulder, is received within an internal lumen of threaded screw 908. In some embodiments, elbow extension 910 is freely received within threaded screw 908 such that rotation of the screw does not affect rotation of elbow extension 910. FIG. 9D illustrates a proximal portion of elbow extension 910 operably received within a rotation gear 914 of a second actuation mechanism 920, aligned proximally (and, in some embodiments, linearly) relative to first actuation mechanism 912. Optionally, in this manner, additional nested extensions (e.g. a wrist extension such as radius 416) are freely received within a more proximal actuation mechanism and operably received within a more distal actuation mechanism.

Figure 10A:
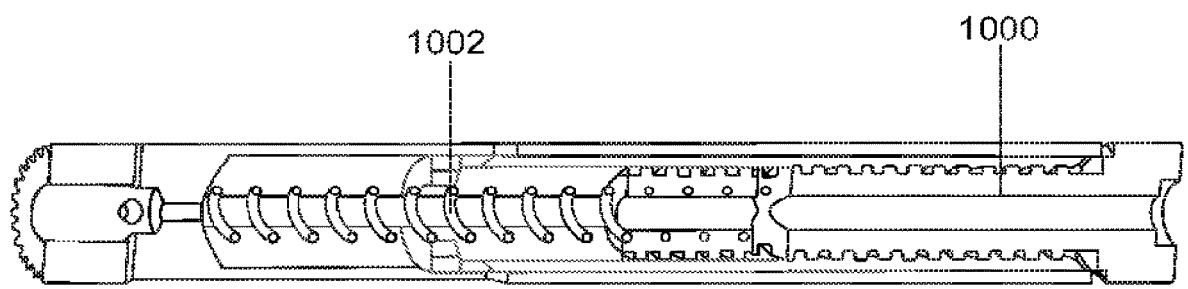
FIGS. 10A-B illustrate clutch mechanisms, according to some embodiments of the invention.
Figure 10B:
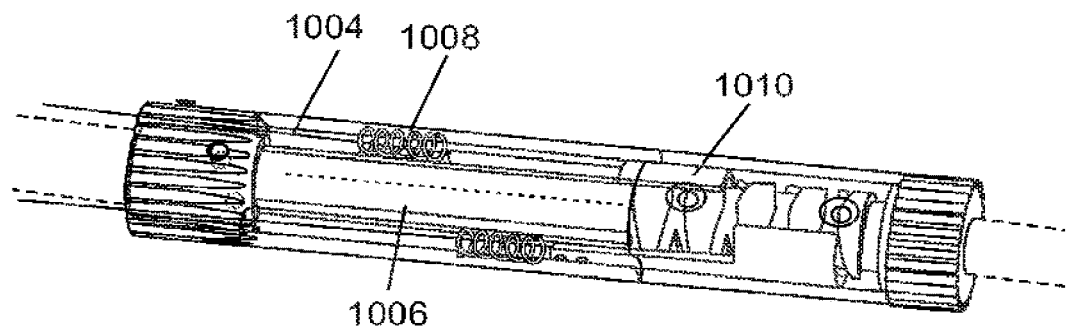

FIGS. 10A-B illustrates a clutch mechanism, according to some embodiments of the invention.

In some embodiments, an elastic element such as a spring is used for setting a minimal and/or maximal actuation force, according to some embodiments.

In some embodiments, as shown for example in FIG. 10A, threaded screw 1000 is coupled to a central spring 1002. In some embodiments, rotation of screw 1000 applies torque and/or tension to spring 1002. Optionally, when the applied force tensions (e.g. linearly pulls and/or twists) spring 1002 beyond its elastic limit, the spring yields and further rotation of screw 1000 is no longer effective to move elongated elements 1004 and 1006 (shown in FIG. 10B).

Additionally or alternatively, one or both of the elongated elements is coupled to an elastic element such as a spring 1008, for example attached between a proximal end of the elongate element and the half-nut 1010. In some embodiments, rotation of screw 1000 actuates linear movement of the elongated elements, for example pulling elongated element 1004. Optionally, when an elongate element such as 1004 is tensioned above a certain threshold, spring 1008 yields and rotation of the screw is no longer effective to move (e.g. pull proximally) the elongate element.

Figure 11A:
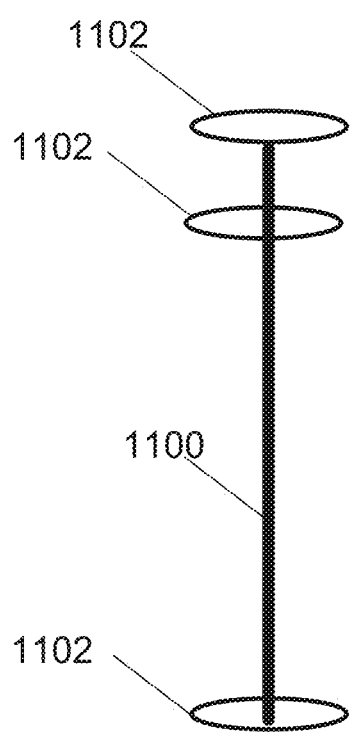
FIGS. 11A-B illustrate various configurations of an actuation mechanism, according to some embodiments of the invention.
Figure 11B:
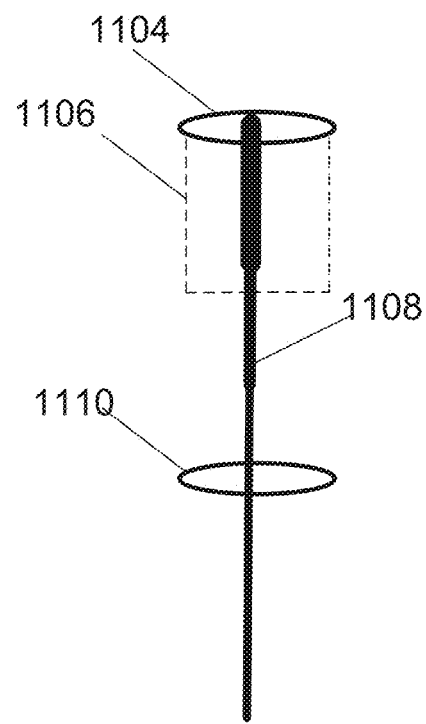

FIGS. 11A-B illustrate various configurations of an actuation mechanism, according to some embodiments.

FIG. 11A illustrates a configuration in which three actuators 1102 are configured to manipulate a shaft 1100 (or a distal extension thereof). In some embodiments, actuators 1102 include, for example, a rotation actuator, a bending actuator, a linear actuator configured to move the shaft back and forth, or combinations thereof (for example, two bending actuators and one rotation actuator, etc).

FIG. 11B shows a telescopic configuration in which, for example, an actuator 1104 is configured to extend shaft portions distally and/or approximate shaft portions proximally, for example using elongated elements 1106 attached to a protruding end of a shaft 1108.

In some embodiments, an actuator 1110 is shaped and/or sized such that the shaft or only some portions thereof is slidably received in it, for example the shaft or portion thereof can be moved back and forth through the actuator.

FIG. 12A is a flowchart of a method for maintaining calibration of a surgical arm, according to some embodiments of the invention.

In some embodiments, surgical device arms are initialized to a straight position, in which segment long axes are parallel (e.g. collinear), for example as shown in FIG. 12B. Optionally, a direction of bending 1200 of first arm segment 1202 is lined with a direction of bending 1204 of second arm segment 1206.

In some embodiments, surgical device arms are provided in a straight position e.g. factory calibrated to a straight position. In some embodiments, a jig is used to straighten surgical device arm/s.

In some embodiments, a configuration of the actuation mechanism(s) is set in accordance with the calibrated configuration of the arm, for example, the gears are rotated to a position in which all arm portions are straightened relative to each other.

In some embodiments, one or more mechanisms are provided for maintaining a calibrated position of the arm, for example during insertion of the arm (or extensions thereof) to the motor unit 1212, for example as shown in FIG. 12C. In some cases, arm extensions may be unintentionally rotated, for example when moved against the motor gear 1214 during insertion. In some embodiments, one or more mechanisms are provided to prevent such movement.

Optionally, during insertion, motor gear 1214 is allowed to move (for example so as not to interfere with advancement of the arm (or extensions thereof) proximally), and once the arm is seated in position, the motor gear is locked until further activation. In some embodiments, motor gear locking and/or releasing is electrically controlled by a micro-switch connected to the motor.

In the exemplary mechanism described herein, actuation mechanism(s) of the arm are temporarily fixated (1208). In some embodiments, temporary fixation is achieved by one or more elements configured to interfere with rotation of the gears (e.g. rotation and/or bending gears).

In some embodiments, for example once the arm is fully received within the motor unit, the temporary fixation of the gears is released (1210). Optionally, fixation is released in response to manual operation by the user, for example closure of a cover door of the motor unit. In some embodiments, the interfering elements are moved away from the gears, for example using spring-based actuation.

In some embodiments, the motor unit comprises one or more calibration discs, configured for indicating whether a gear has moved, for example during insertion of the arm.

FIGS. 13A-E illustrate a mechanism for maintaining calibration of a surgical arm, according to some embodiments.

Figure 13A:
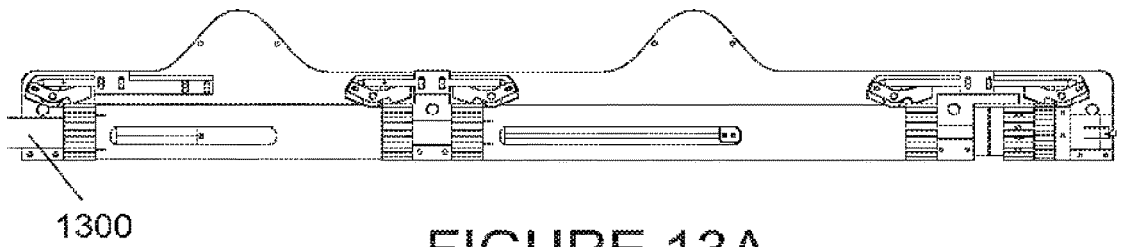
FIGS. 13A-E illustrate a mechanism for maintaining calibration of a surgical arm, according to some embodiments of the invention.
Figure 13B:
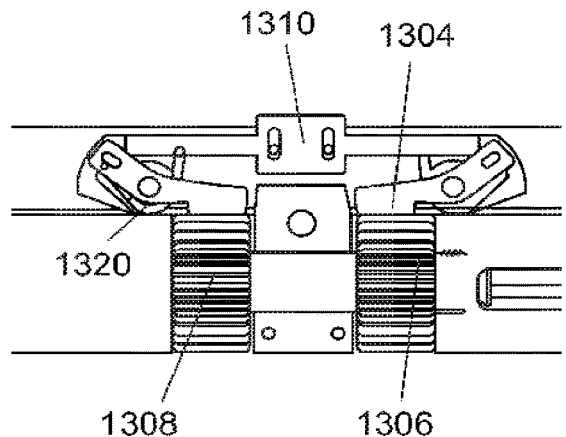

In some embodiments, for example during insertion of arm 1300 to the motor unit 1302, interfering elements 1304 are moved to a position in which they lock gears of the actuation mechanism (e.g. gears 1306, 1308), preventing the gears from rotating, for example as shown in FIGS. 13A and 13B. Optionally, the interfering elements are moved to the locking position by a spring and/or other elastic element 1320 (positioned behind interfering element 1304).

Figure 13C:
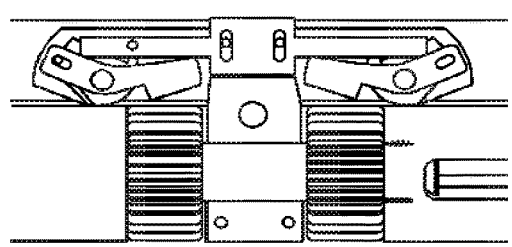

In some embodiments, a lever 1310 is coupled to the interfering elements. Optionally, when lever 1310 is pushed on, for example as shown in FIG. 13C, the interfering elements are moved to a position in which they no longer interfere with rotation of the gears.

Figure 13D:
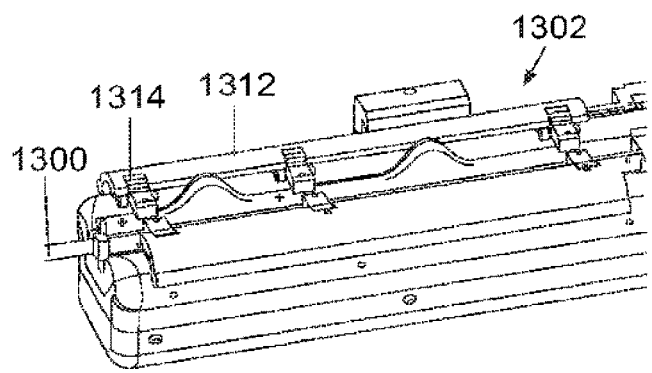

In some embodiments, lever 1310 is pushed on (and/or elevated) in response to closure of a cover door 1312 of the motor unit, for example as shown in FIG. 13D. Optionally, locking of latches 1314 (optionally manually, e.g. by a physician or a nurse) applies pressure onto lever 1310, releasing the interfering elements from the gears to provide for articulation of the arm.

Figure 13E:
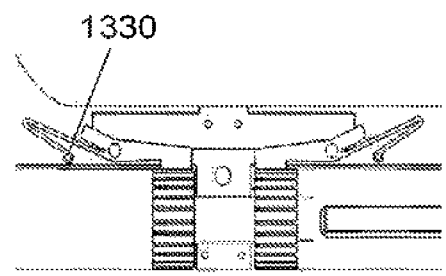

FIG. 13E shows an interfering element comprising an elastic element 1330 which springs into a locked or released position.

Figure 14A:
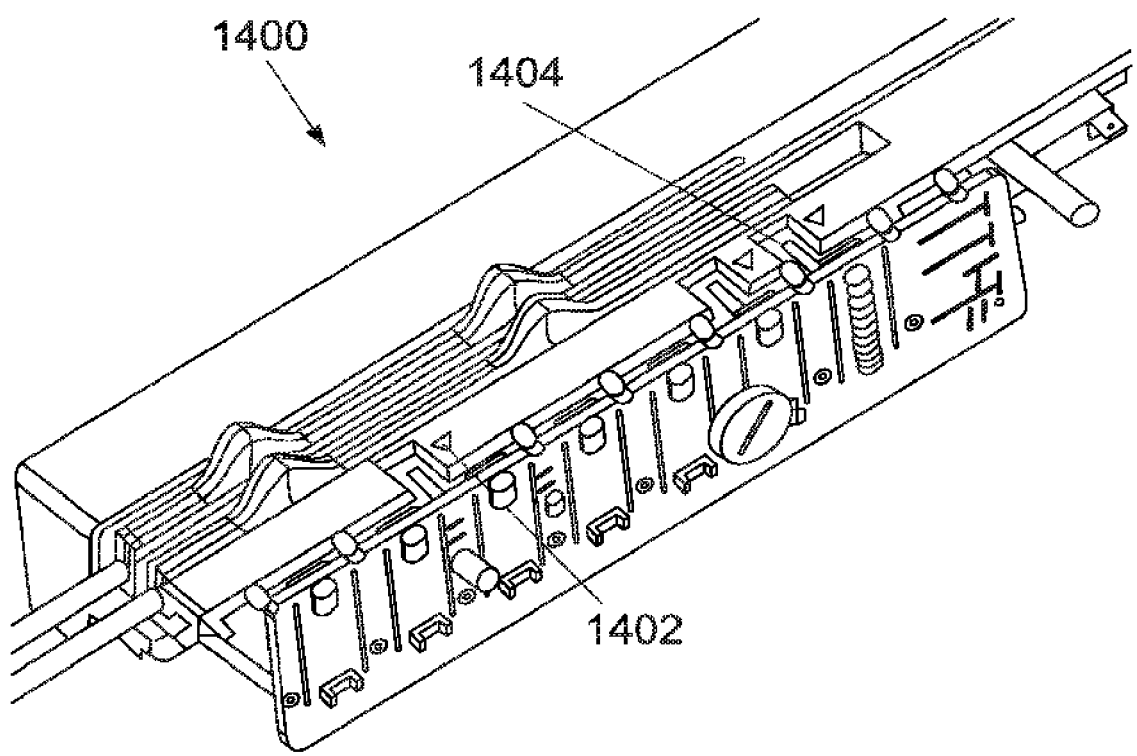
FIGS. 14A-B are an inner view of the motor unit (14A) and an outer view of the motor unit (14B), according to some embodiments of the invention.
Figure 14B:
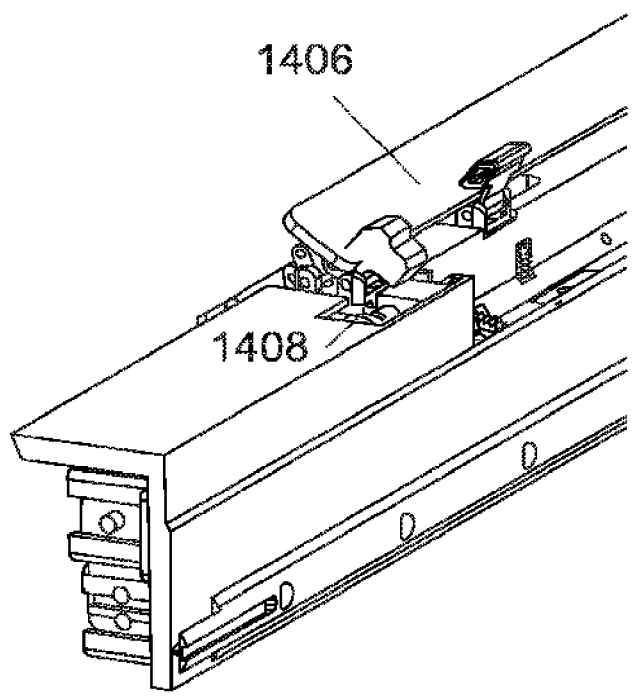

FIG. 14A is a view of the motor unit 1400 showing an exposed inner portion of the motor unit, according to some embodiments. FIG. 14B shows an outer view of the motor unit in which a cover door of the motor unit is open.

In some embodiments, a user (e.g. physician and/or nurse) is provided with internal access to the motor unit. In some embodiments, for example during a power outage, manual override by the physician is enabled. Optionally, the user can access the motor(s), for example to manually operate to the motor gear 1404. In some embodiments, one or more directing arrows 1402 are marked on the motor unit housing, optionally indicating a rotation direction in which the gears need to be rotated in order to straighten the arm.

In some embodiments, the cover door of the motor unit 1406, see FIG. 14B, is configured to automatically lock, for example during power outage. Optionally, a solenoid bolt 1408 locks the cover door. Optionally, the solenoid lock mechanism can be manually overridden, for example by opening the cover door to allow access to at least some of the internal components of the motor unit.

In some embodiments, the solenoid lock mechanism is configured to prevent unintended removal of the arm(s) from the motor unit. In an example, cover door 1406 cannot be opened until solenoid 1408 is released, for example by the physician, optionally via the user input device.

In some embodiments, control of arm insertion and/or removal is limited to a user, for example only the physician can control opening and/or locking of the solenoid lock mechanism, for example via the user input device.

In some embodiments, for example during a power outage, power supply is provided by a battery.

Figure 15A:
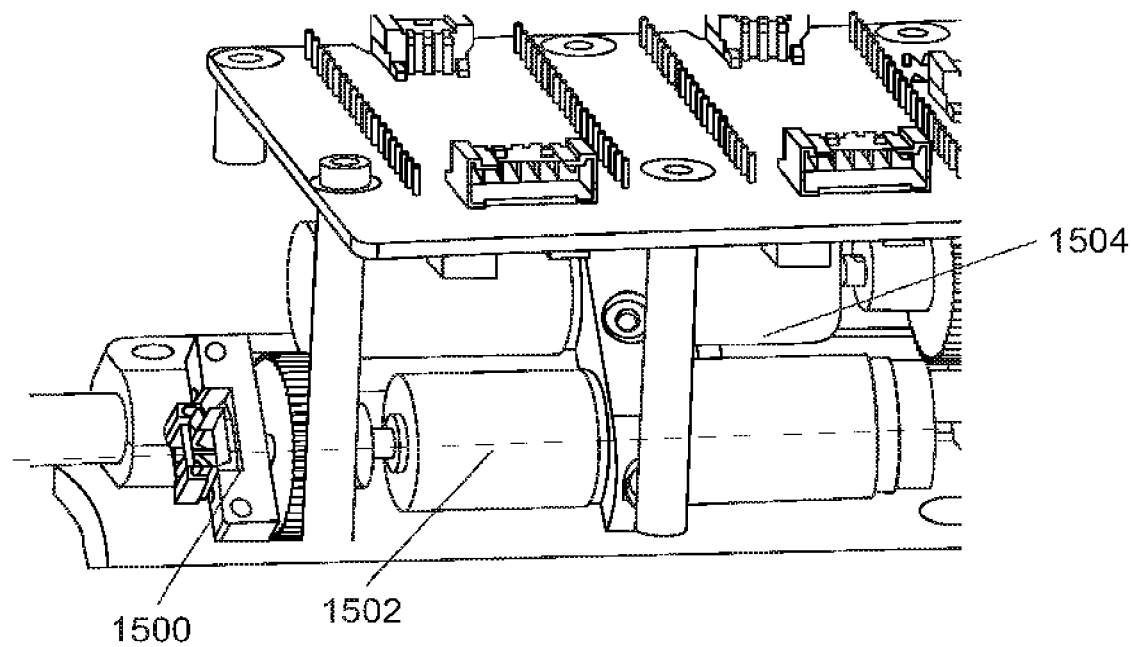
FIGS. 15A-B are cross section views of the motor unit showing safety-related electrical components and position sensors, according to some embodiments of the invention.
Figure 15B:
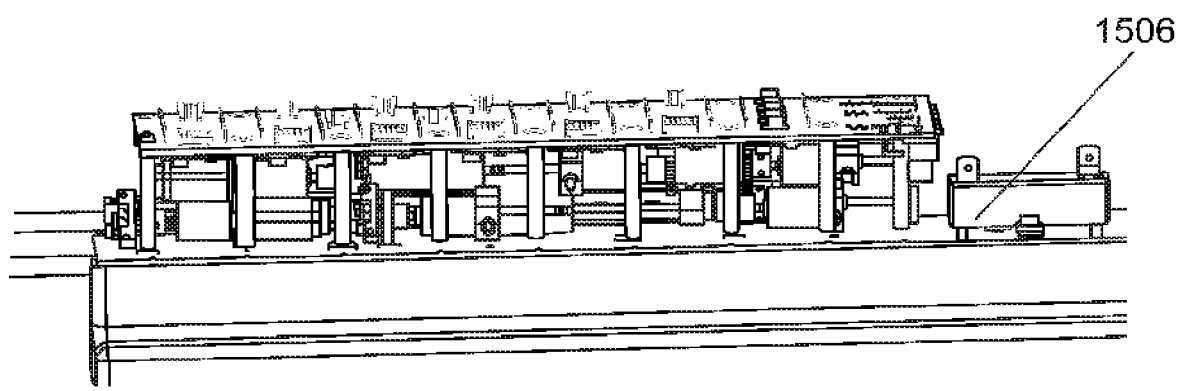

FIGS. 15A-B are examples of safety-related electrical components of the motor unit, according to some embodiments.

Referring to FIG. 15A, in some embodiments, cross-control over motor activation is provided. In some embodiments, a safety sensor 1500 is operably coupled to a first motor 1502. In some embodiments, control over safety sensor 1500 (e.g. on/off activation) is performed by a controller of a second motor, for example motor 1504. Optionally, the controller detects malfunction of the first motor.

Referring to FIG. 15B, in some embodiments, power delivery to the arm (e.g. to an electrocautery instrument attached at a distal end of the arm) is controlled with the aid of a relay 1506. Optionally, relay 1506 restricts current delivery when the electrocautery instrument is mistakenly attached to an arm, for example attached to the left arm instead of the right arm or vice versa. In an example, a physician defines (optionally via the user input device) that monopolar energy is delivered to an arm defined as the right arm, and bipolar energy is delivered to an arm defined as the left arm. Optionally, relay 1506 is configured to detect a mismatch, for example that the bipolar electrocautery tip was attached to the arm defined as the right arm instead of the arm defined as the left arm, and the electric current is ceased.

FIG. 16 is a simplified side view of a portion of a motor unit including elements for supplying electric power to an end effecter of the surgical arm, according to some embodiments of the invention. In some embodiments, one or more mechanisms are incorporated in the motor unit for ensuring that the electric power supply is not effected by a current position arm position. Alternatively, the electric power supply is effected by a current arm position.

In some embodiments, portion 1630 is coupled to an end effecter such that, when 1630 is rotated, it rotates an end effecter, for example, portion 1620 is coupled to hand tool 424 of FIG. 4A. In some embodiments, gear 1632 actuates the end effecter, for example, rotation of gear 1632 opens and/or closes jaws of a grasper end effecter. In some embodiments, contacts 1622 and 1624 provide electric power to ring portions 1626 and 1628 respectively. In some embodiments, one of contacts 1622, 1624 provides positive voltage and the other negative, providing bipolar power supply. In some embodiments, each of ring portions 1626 and 1628 are electrically connected (e.g. through wires running through 1630) to an end effecter, where one of the ring portions is coupled to one side of a grasper and the other to the other side of a grasper.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An actuating mechanism comprising:
    a first gear operably coupled to a threaded screw, said first gear configured to rotate said screw around its screw axis;
    first and second rider elements coupled to threading of said threaded screw, wherein said first rider element is attached to a first elongated element and said second rider element is attached to a second elongated element;
    a shaft having a long axis, said screw axis of said screw and said long axis of said shaft being colinear with each other;
    a second gear configured to rotate said shaft around said long axis of said shaft; and
    a housing in which the threaded screw is received, the housing being disposed around said long axis of said shaft, the housing having therein designated elongated grooves within which each of the first and second elements are positioned, said elongated grooves being configured such that actuation of the second gear does not twist the elongated elements about the long axis of said shaft;
    wherein rotation of said threaded screw moves said rider elements in opposing directions along said long axis of said shaft, tensioning said first elongated element and releasing tension of said second elongated element or vice versa.

2. The mechanism according to claim 1, wherein rotational movement of said rider elements around the screw is limited by one or more protrusions configured on an internal face of the housing.

3. The mechanism according to claim 2, wherein (i) each of said first and second elongated elements is respectively and proximally attached at to said respective rider element, and (ii) each of said elongated elements is respectively and distally attached to said shaft at a location distal to a flexible joint of said shaft.

4. The mechanism of claim 3 wherein said second gear is located distal to said first gear.

5. The mechanism of claim 4 wherein both of said first and second riders are located distal to the first gear and proximal to the second gear.

6. The mechanism according to claim 1, wherein (i) each of said first and second elongated elements is respectively and proximally attached to its respective rider element, and (ii) each of said elongated elements is respectively and distally attached to said shaft at a location distal to a flexible joint of said shaft.

7. The mechanism of claim 6 wherein said second gear is located distal to said first gear.

8. The mechanism of claim 7 wherein both of said first and second riders are located distal to the first gear and proximal to the second gear.

9. The mechanism of claim 1 wherein said first and second riders are both disposed in a location, along the shaft axis, that is in between the first and second gears.

* * * * *